United States Patent [19]
Fisher

[11] Patent Number: 5,882,874
[45] Date of Patent: Mar. 16, 1999

[54] RECIPROCAL SUBTRACTION DIFFERENTIAL DISPLAY

[75] Inventor: Paul B. Fisher, Scarsdale, N.Y.

[73] Assignee: The Trustees of Columbia University in the City of New York, New York, N.Y.

[21] Appl. No.: 32,684

[22] Filed: Feb. 27, 1998

[51] Int. Cl.⁶ ....................................................... C12Q 1/68
[52] U.S. Cl. ............................................. 435/6; 435/91.21
[58] Field of Search .......................... 435/6, 172.3, 91.2, 435/91.21

[56] References Cited

U.S. PATENT DOCUMENTS 5,599,672  2/1997  Liang et al. ................................. 435/6

*Primary Examiner*—James Ketter
*Attorney, Agent, or Firm*—John P. White; Cooper & Dunham LLP

[57] ABSTRACT

This invention provides a method for identifying differentially expressed nucleic acids between two samples, comprising: a) selecting a first and second nucleic acid sample; b) producing libraries for the first and second nucleic acid sample; c) performing reciprocal subtraction between the libraries to produce two subtracted libraries; d) amplifying the two subtracted libraries; and e) comparing the two amplified subtracted libraries to identify differentially expressed nucleic acids. Also, this invention provides the above-described method, wherein the 3' primer used in the PCR amplification is an oligo dT 3' primer. This invention also provides the above-described methods, wherein the comparing of step e comprises using a gel to separate the nucleic acids from both of the libraries. This invention provides the isolated nucleic acid identified by the the above-described methods, wherein the nucleic was not previously known to be differentially expressed between the two samples.

18 Claims, 11 Drawing Sheets

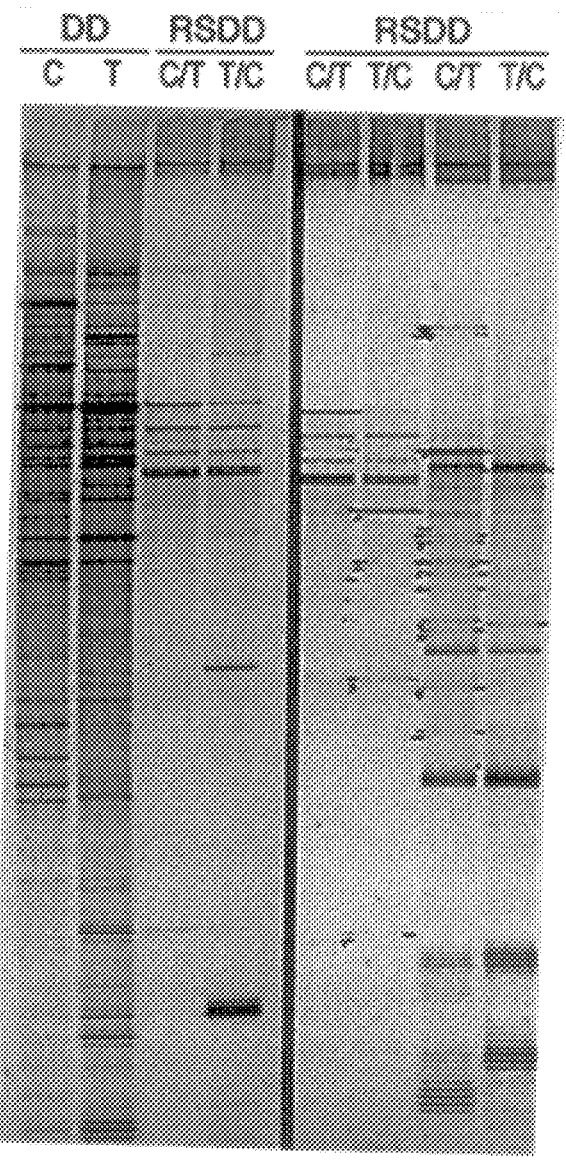

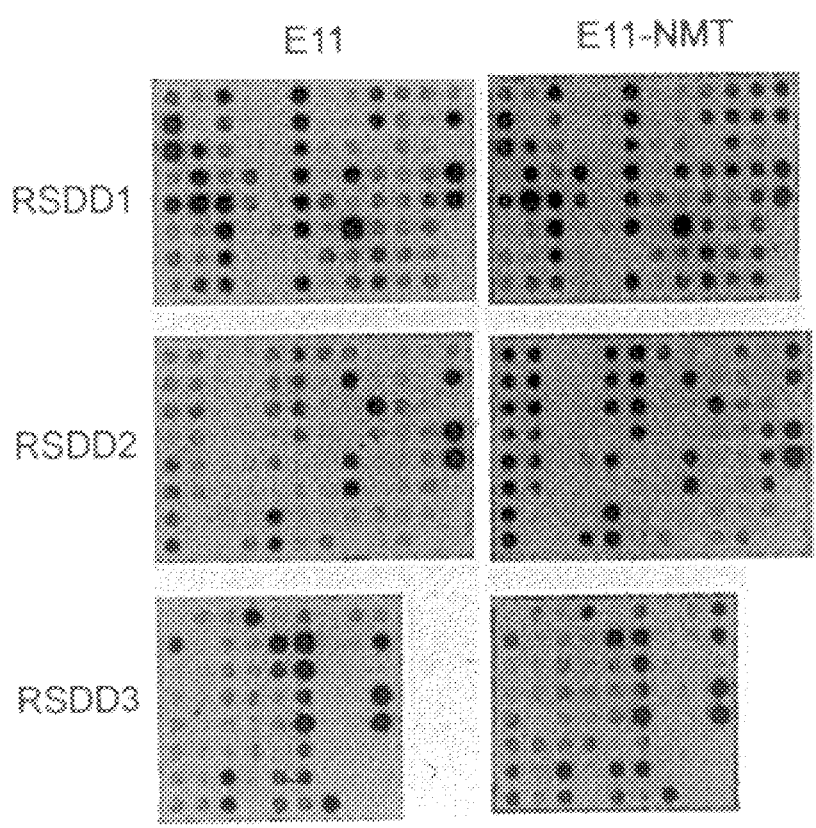

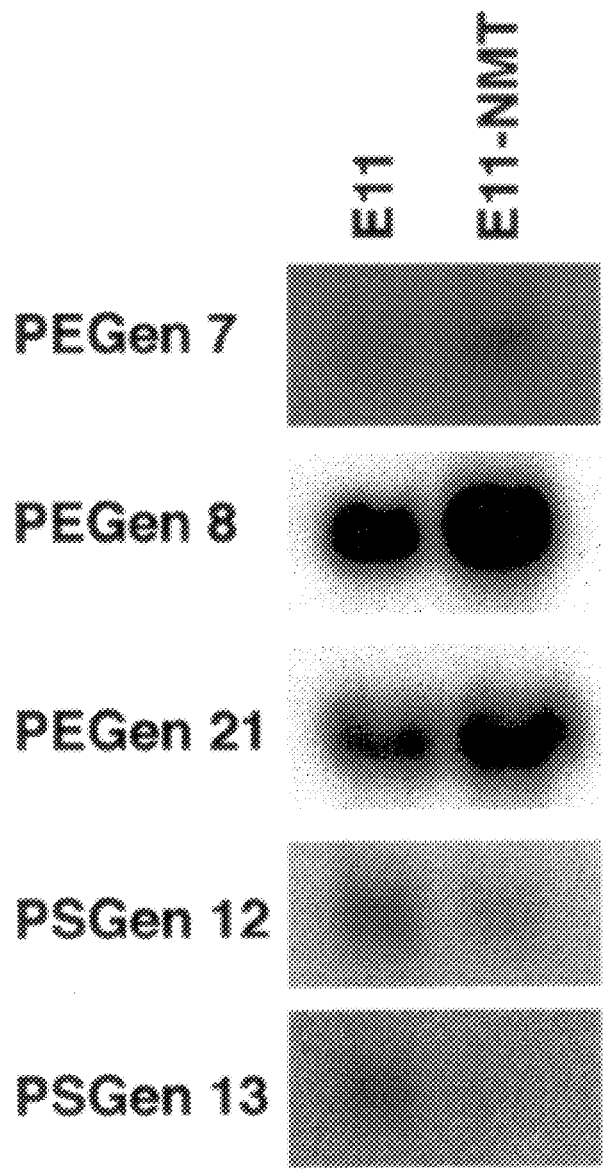

FIG. 5
PEGen 7-90% homology to human HPV16 E1BP

```
TAAANCGGTG GTACTGCTGC ACGGTCCTCC GGGTACTGGA AAGACATCCC
TTTGTAAGGC ATTAGCCCAG AAACTGACCA TCAGACTGTC AANCAGGTAC
CGGTATGGCC AGTTAATTGA AATAAACAGC CACAGCCTAT TTTCTAAGTG
GTNTTCAGAA AGTGGCAAGT TGGTAACTAA GATGTTCCAG AAGATTCANG
ACTTGATTGA TGATAANNAA NCTTTGGTGT TTGTCCTGAT TGATGANGTA
AGCACTCANN GGTACTCATT CTTNGTCTGC ATTGCCTCTT GCTATTACTG
CCTGATCCCT CTCATTTGGT TCACTGTGTC GCNANCTCTT TTCTATGGAT
CTTTTCCNAN CCACCCGTTT C
```

FIG. 6
PEGen 8-Rat phosphofructose kinase C

```
GTGACGTAGG GTCTGTTGCG TCAATGGTTA TAGCAAGTGA TGCTCTCTGA
TTATTACTGC TGACAATACT CGGCCAACAA TTCTTGCATA GAGTGCTGAT
AAATAACTAT GTTACAAAAA GGGGTGGTCC CTGGAGAACA TTACAGGCTT
CCCTAGGTAA GTGTGCAGGT CAGGAGACGG CATATTCAAT CAGATGGCTG
ATAGTTCTCC GTGGTTATGC ACCGGCTCCA GCTTGCCTAC GTCAC
```

FIG. 7
PEGen 13-Novel

```
GCAGCATGAT GAATTTAATG CAACAGTCAT AGCAGGGCAA GGGGAGAGAA
AGGCAGATGG ACTATCTGCA TCATCAAGCG AGGGCTTGTG TCGGCGGCTA
TGTGCAGAGA CGAGCAGGGC GAGGCACTTA AAAGCTGCTN GATGAAAATC
CACCCAGGAG AANTCTGGGC CTACGTCA

TGACGTAGGC CCAGACTTCT CCTGGGTGGA TTTTCATCCA GCAGCTTTTA
AGTGCCTCGC CCTGCTCGTC TCTGCACATA GCCGCCGACA CAAGCCCTCG
CTTGATGATG CAGATAGTCC ATCTGCCTTT CTCTCCCCTT GCCCTGCTAT
GACTGTTGCA TTAAATTCAT CATGCTGCCA AAAAAAAAA A
```

FIG. 8
PEGen 14-Novel

```
GCCATAAATA CACTTTATTT CATTCGAAAT GCATAATCAC ACTGGGAGCA
CTCCCTTTGG AGCACTCCTC TAGCAGCAGG TCCGAAGTGC TCCAGCATCG
TCAGCTGGCT CCAACACCTA CGTC
```

FIG. 9
PEGen 15-Novel

```
TTTTTTTTTT TTTGGAAACA GAATAAAGTG CTTTATTCTC TGGCTGGCTC
TCCTACGTCA C
```

FIG. 10
PEGen 21-94% homology to mouse FIN 14

```
TCGGCGATAG CATTGGAGCA AGTCTTATCA GCAAGCAATG TTTTCAGTTA
TGTTTCAAAG TTAAGAATGG GTTTAAACTT GCTGAACGTA AAGATTGACC
CTCAAGTCAC TGTAGCTTTA GTACTTGCTT ATTGTATTAG TTTANATGCT
AGCACCGCAT GTGCTCTGCA TATTCTGGTT TTATTAAAAT AAAAAGTTGA
ACTGCAAAAA AAAAAA
```

FIG. 11
PEGen 24-Novel

```
TTTTTTTTTT TTTTTTTTTT TTTTTTTTTT TTTTTTTTTT TNGCCAGGCT
ATGTCTCAGA CTTTATTATT ATTATTATTA TTATTATTAT TATAAATAAA
ACATGTNCTT TCAATTAGGT TACAANAGTA TTTATCTCCA TAACGCTTCT
TCATACATCC TTAGTTTTGG ATTAAAGTAC CATCCACCCC AACTCAAACT
GTAACCCCCA GTAATCCCCT CTAACGTGGA AATTTCTGGT TTAACAACTC
AGTTAACTGC CCCACAAACA GTGGGAGGCC GCTCTTGCAT GGCTATGCCA
CGTAACCCTT CACTGCTTCA CTTCTTCGCT GGCT
```

FIG. 12
PEGen 26-Rat poly ADP-ribose polymerase.

```
GACCGCTTGT ACCATCCAAC TTGCTTTGTC TTCTGCAGAG AGGAGGCTAA
AGCCCTTGAG CTGGCTGGCA CTGTACTCAG GCCGGAAGCC CAGCTCGTCC
CGGTTCTTGA CAAAGCAAGT TGGATGGTAC AAGCGG
```

FIG. 13
PEGen 28-Novel

```
TGCCGAGCTG GGTATTGTGA CGGTTGATAA TGGCGGCATC ATGTTGCCAG
GTACCGGGTA AGCAGACCTC AGAGCACAGC TTATTGTCCA GTGCTTTCAC
GCTCGCGACG TCAAAGTCAT TGTTATTGTC ACACTCCATG CCTAGAAATG
CGCATGTCCT CTGGCCATCT TCTTGCACAG GGGATCTGTC CTCTTCCTCC
ATGATATCAT TTCCCTCTGC ATCCTGCTCT CCAGCTGGAA GGCCAGCAAA
ATTGCTGTCT GGGGACTCTG CTGGGGTCTC CTCCTCTTCT GAAGGGGCCC
TGCTAGCAGC TCGGCA
```

FIG. 14
PEGen 42-Novel

```
AGGGGTCTTG ATGGACTTGG GTCGGACATC TTAGTGACCT GTGAATTCTT
CTGTGGAGGC TGAGTCTCAC GTAGCCGAGT TTAATATCTG TGCTATTTAC
TAAAGTATCT GCCACCAAAT TGTACCAACT CATAGTTTTA TATGAATGTT
GATGAGTCTG TATCATAAAT AGAATTGTTG ATACATCCTT AATTTGTGCA
ATATTGTATG AAGAAGATTG TTATCAATTA AAACCACGCC TCTTTATGAT
CCTNNAAAA AAAAAAAAAA AAAAAAAAAA AAAAAAAAA AAAAAAAAA
AACCNCCTCA AATCCATNGG TTCTAACCCA AAACCCT
```

FIG. 15
PEGen 43-Novel

TTTTTTTTTT CATACACCAT CAAACCAATT TTATTTCTAT AGCAACGTTT
CTCACGTCTG AACCTGAGAA TAAGTCACCA GCTCTTGACA GTAAACATGG
GCCCTATCAA ATTATATTAG ACTCCTCAGT GTCCCGCCAT GTGGCCTTGC
ACCAAATCAA TTAGTTTGAG GGCCAAAATC CTGTTGGGTT TCAAATAAAG
TGTCAGGTCA TAAGGAGGGG GAGGGACTCA ATTCATGGGA ACATTTTTAC
CTGTTCAAAT AGATAAACTG AATTGCCCTA TCTGTGGTCA CCTGGATCCA
AGACCCT

FIG. 16
PEGen 44-Novel

CCCTGACGAT AAATGGTAAG GAACTTTTTT TTTTTTTTTT TTTTTTTTTT
TTTTTTTTNC GAAATAAACA AACACAGCTT ATTATTTGGG GGAACATTAA
NTTCTATAAN TGAACACAAA ANAAAATTAA NANTTAATGG GGGGGTANAA
GGGACTTTGA ATCTATCTGG TATCATGACA TTGAAGCANA NACCTGANTG
ACCAGAAAGA GAGAGAGAGA GAGAGAGAGA GAGAGAGAGA GAGAGGTTTC
ATATGAGCTA GTGTTACAGG CTTTATTAGT CTATTAGTCA GGGACC

FIG. 17
PEGen 48-Novel

AATCGGGCTG GATGGGTGTA TCCGGCACTG TTTCGTAGCG GCAGCAACTG
GGTGCTTCTA TCTGAAAGCG GGCTTCACAA AAACTACTGC GCCACCCGAC
TCGCTGCGGC ATCGCCCGGT GGCGAGTACC GTATCGCCTT TCCTGGTGCA
GAAGAAGTGT TTACAGGAGG CGGTCATTTA CCGCAATCTG ATTCTGTTTT
TTATTCTCCC TGGCGGGTGA TCGCGATCGG CAGTTTGAAA ACGATCGTTG
AATCCACGCT CGGGAATGAT GTGGCTTCGC CGCCAACGCT TACTGACATT
TCATTTGTAC AGCCCGATT

FIG. 18
PSGen 1-80% homology to *B. taurus* supervillin

GCCGAGCTGT GTAAAACCAT CTATCCTCTG GCAGATCTAC TTGCCAGGCC
ACTCCCAGGG GGGGTAGACC CTCTAAAGCT TGAGATTTAT CTTACAGATG
AAGACTTCGA GTTTGCACTC GACATGACCA GAGATGAATT CAACGCACTG
CCCACCTGGA AGCAAATGAA CCTGAAGAAA GCGAAGGCC TGTTCTGAGG
GTGAGATGAC AGCCACAGAG AGGTCACTGC CACTAGACCA GAAAGTGGAT
GGAGATATAT ATTTGGACTG GTGTTTTTTT CTGTCAG

FIG. 19
PSGen 2-91% homology to human HTLV-1 Tax interacting protein

```
ATCGGGCTGC AGATTGGAGA CAAGATCATG CAGGTGAACG GCTGGGACAT
GACCATGGTC ACTCATGACC AGGCTCGGAA GCGGCTCACC AAACGTTCGG
AGGAAGTGGT CCGCCTGCTG GTGACTCGGC AGTCTCTGCA GAAGGCCGTA
CAGCAGTCCA TGCTGTCATA GCTGTAGTCA GCCTAGACTT CTGCCCACTG
ACCTTTTNGG GCACTGAGAA CACATCCACG CTCTGTCTGT ATCTAGTTCT
GGCTTCTGCT GTGTGCTANG CCCCAGCTCT GAGGAGTAAC AGCTGATCCC
AAAGGTCCAA GCCAACCTTC TTACCCCTCA GCCCCCANCC CGAT
```

FIG. 20
PSGen 4-Rat proteasome activator

```
TTTTTTTTTT TTTGGGCAAC TATGTATTTA TTGTGTTTGG AAGGCAGAGT
GAGGGAGGAG ACCCCAGCAG GAAGAAGACT GGGTGCAGTC TAGAGTTCCT
AGTCAAGAGT AGGAAGGTTT CTGTTATACC CATCATAGAA CGAGAGAGGG
GGCTCAATAG ATCATCCCCT TTGTCTCTCC ACGGGCTTC TTGAGCTTCT
CAAAGTTCTT CAGGATGATG TCATATAACA CAGCATAAGC GTTACGGATC
TCCATGACCA TCAGCCGGAT CTCCTGGTAT TCCGCCTCGT CCAGCTCGGC
```

FIG. 21
PSGen 10-Rat Ferritin Heavy Chain

```
AANATCTGCT TAAAAGTTCT TTAATTTGTA CCATTTCTTC AAATAAAGAA
TTTTGGTACA AATTAAAGAA CTTTTAAGCA GATGTTTTGG TGCAACTAAT
AGAAAAGATA AAGGCAGCCT GACATGCATG CACTGCCTCA GTGACCAGTA
AAGTCACATG NCCTTGGAC GTCAGCTTAG NTTTATCACN GTGTCCCAGG
GGTGCTTGTC AAAGAGATAT TCTGCCATGC CAGATTCAGG GGCTCCCATC
TTGCGTAAGT TGGTCACGTG GTCACCCAGT TCTTTAATGG ATTTCACCTG
CTCATTCAGG TAATGCGTCT CAATGAAGTC ACATAAGTGG GGATCATTCT
TGTCAGTAGC CAGTTTGTGA AGTTCCAGTA GTGACTGATT CACACTCTTT
TCCAAGTGCA GTGCACACTC CATTGCATTC AGCCCGCTCT CCCAGTCATC
ACGGTCACNT A
```

FIG. 22
PSGen 12-Novel

```
TGACGTAGGG CCGAGAGCAA CAAGCACAGA ACTCCTTCTC CAGTTTCACC
CTGATGAAGT TGAGGCACTC TTCTGCACTG GGAGGGGCCA GCCTGGGGGC
CAGGCACATT GGACACCACC TTCCCATGGA CTACAGCGTC AATGCCATTG
CCTTCTATTC CTATACCTTC TAGGGGCTGC CCCTCTTCCC ATTCAGCCAA
CACTGAGTGT TGGGAGATTT CTCTTTTTTA AAAACACATG AGAAAATAAA
TGCACTTTAC TCCCTCCCCA AAAAAAAAA
```

FIG. 23
PSGen 13-Novel

```
GTAGGCAATA AAATGTTTTC AGAGGTGCGA AAAAGCTTTT GTTTTCTTAA
ACCATTCTTA GTCTCTGCCA CACTTGACAC TCCGTCAAAG TGAGAAGCGA
ACTAAAGACC AACTGCGGTG GAAAATATTA TGTTTATGTA ATAAAAAAAA
ATCATGTAAC TGCAAAAAAA AAAAAAA
```

FIG. 24
PSGen 23-Novel

```
TGCCGAGCTG AAAACATACA TCCGCACCGG GTTGAGATAG CTGGCCCTCC
GTCCCCGGGC ATACTCTTTG GATAAGAACC CCGGCCTTGT TACCAGGTAC
CGGAGTGAGC TGAAAAATTT ACCGTCGAAA TGGGTGATGT CCTGGAAAAA
ATGGTTCACC AGCTGCCAGG CAGATTCTTT GGGTTCCACA TTTTCCTGCC
CACAGATGTG GCAGAAGCGG TCAAGTAATG CAGCATTACA ATTGAGGCAG
ATCTTTTCTT TTCTTTCCTT GGAGTGGCTC AACCAGCGAT TTTGGTTAAA
AATAATCAAA AAAGCGACGG CAAAACTTTT GTTATATTCC CGCCTGTGGC
ATTTGAACTG TGCCCGGCAA CCGATAACT TTTAATTTTG AAAATAAAAT
GCATACTAGA TTTTTAGCGG TTGCCTCCTG GCCATTGCTT CAGGCGCCNG
CACAGCGTCA GCCCAGTTTT ACCACNANGA ATATCCTAAG CGTTGAAACA
GGGCACAGCC GAAAAAAACN CTGGCNACAA AAAANATCCG GACATCCTTT
TTCCAATTTT GAAACCGAAN GCNCGCAAAC NAAGGTTCTT CGGGAAAAAA
AATCGCCAAA ATACNCGANA TCAAACTNTC CAA
```

FIG. 25
PSGen 24-Novel

```
TGCCGAGCTG GGGGGAGTTC CAGGAATTTG TGGACTATTT CCAGGAGGAA
TTGAGGAATC TAGAAGTAAT AAGAACTTCA CAAGTAGAAC AACAGAGTTA
ATTGACCTCT ATCCTTAAGA GTTACCAGAG AATTATTAAA AAACTAAAGA
ACAATCAAAG CCTGGTCCTG TGCCACCACC CAAAAACATG TATAGCCTAT
GTGCAGCTCG GCA
```

FIG. 26
PSGen 25-Novel

```
CTCANAGGGC NNNTTNGNGG NCNTCATGCN CCAGGNTCCN NCCCCCANAN
GANCNNCCNG GTAAACTACA CNGGAGTACT TAAGTGGACA NNCCACATGC
GANGGNCAAG GGGATCACCN TCNCTCCTNC AGNCTNTNCG TGNCTCTCCT
GTNCNTNCAC TGCCNCANAA NGGANGCNCN NNCTCCTATC TGTNTACAGN
AAACNTNGCN CTNNCTCTAA GCTCNCCCAC TNTGTGGAAA GGCNATGTGT
GCGTGCCTCT CCCCTATCAC GGCNGTTGC NAAANGGGGA TGTNCTGCNC
GGCGATGAAG TTNGGTCACT CCATGTTTCC CAGTCCNACC TGTTAGACNA
AGNATTGNAN TGTGATACGA CTCNCTGTAA GGGGANTNGC GGACCCAGTA
TGTTTGGCCC NACNNCCACT TCTTTAAATG GTGGCTAACG GCGCTTCCTA
GNATAAACAC TATTGGTCCC CCCCTCTGCA GNACCCNTTA CTTCCGNANA
AAAATTGTTG TCNTGATCCG CGACAACCAC ACCGTCTGTN GNTTTTAGTT
GCAACNCNNA TCNCTCCAAA AAAGTTTCAG AAATCTTCAT TTTCCCNGGT
TGAGCCCNTG ACAAACCCCT NAGGATTTGT CGAATGTAAA GTCTCCNGAT
CTTCAATAAA NNTCCAAAAG NCTANCGAT
```

FIG. 27
PSGen 27-Novel

```
NTCNNCTTNN CNNNGGCTGA TATCNGGCNC TTCNTCCNCG ATCNCAGATA
CNNGCNCACC GGNNNTNTCN GNGGTNATCN TCCNCCATCT CTCNTCCCCG
ACNTGCACTC CGGGTNTNNT ACACNGGACA CTGTATCNNA CAGNAAACCT
NCCCNGGCCC CAGGGATCAC CATNCCTCGN CCCNGCNTGT NTATAANATC
AGGNNNTACA TCNANGAACN NACTATCACN GNTCTCTNTT NNCTCAGTGT
NCACCTTCCA CTNCNGAANC TNNTCGCTNC NCCNCNGTTG GGAAAGGCGA
NCNGTNCCGG CNACATGCCG TTTNCGNCNT CTGNNCACNT GGGGATCTNC
TNCAANGNAA TCAATTNGNG TAACCCACGG TTTNCNCAAT CACTACTTCT
CANNCNANGG CCNTTGAANT GTTATCCCAC CACCANGGGG CNANTCGGGA
CCTNACAATT CATCCTCAGC CGGCCCCAGN CTTAAAAAAT TCAAAGGNCN
CTTGCCCGCN TTNTTNCCTT AGCCCGCCNC CNGACAACAN CCNANNAACA
ACCCCCNNTC TTANGTTGCN NANCCACAG GANNTTGNNA TACCGGGTTT
CCCCNGAAAC TNCTCAANGC CNCCGTTCCA ACCCCGTTA CGAAACCGTN
CCCNTTTCCT TCCGAGNTTG CCTATTAANN CCCCCNAAGT TCTNCTTCGT
TNGNTTCCTC CGAAANG
```

RECIPROCAL SUBTRACTION DIFFERENTIAL DISPLAY

Throughout this application, various references are referred to within parentheses. Disclosures of these publications in their entireties are hereby incorporated by reference into this application to more fully describe the state of the art to which this invention pertains.

BACKGROUND OF THE INVENTION

Changes in gene expression are important determinants of normal cellular physiology, including cell cycle regulation, differentiation and development, and they directly contribute to abnormal cellular physiology, including developmental anomalies, aberrant programs of differentiation and cancer (1-4). In these contexts, the identification, cloning and characterization of differentially expressed genes will provide relevant and important insights into the molecular determinants of processes such as growth, development, aging, differentiation and cancer. A number of procedures can be used to identify and clone differentially expressed genes. These include, subtractive hybridization (5-10), differential RNA display (DDRT-PCR) (3,4, 11,12), RNA fingerprinting by arbitrarily primed PCR (RAP-PCR) (13, 14), representational difference analysis (RDA) (15), serial analysis of gene expression (SAGE) (16,17), electronic subtraction (18,19) and combinatorial gene matrix analyses (20).

Since first introduced by Liang and Pardee (11), DDRT-PCR has gained wide popularity in analyzing and cloning differentially expressed genes. In DDRT-PCR, total RNAs or mRNAs from two or more cell types (or cells grown under different conditions, cells representing different stages of development, cells treated with agents modifying cellular physiology, etc.) are reverse-transcribed with two-base-pair anchored oligo dT primers, which divide mRNA populations into 12 cDNA subgroups. Then, each cDNA subgroup is amplified by PCR with one of 20 arbitrary 10-mer 5' primers and a 3' anchored primer and the PCR-amplified cDNA fragments are resolved in DNA sequencing gels. The combinations of primers are designed not only to yield a detectable size and number of bands, but also to display nearly the complete repertoire of mRNA species.

DDRT-PCR is a powerful methodology in which a vast number of mRNA species (>20,000, if no redundancy occurs) can be analyzed with only a small quantity of RNA (about 5 $\mu$g) (11). DDRT-PCR is often the method of choice when the RNA source is limiting, such as tissue biopsies. A direct advantage of DDRT-PCR is the ability to identify and isolate both up- and down-regulated differentially expressed genes in the same reaction. Furthermore, the DDRT-PCR technique permits the display of multiple samples in the same gel, which is useful in defining specific diagnostic alterations in RNA species and for temporally analyzing gene expression changes. However, the DDRT-PCR technique is not problem free. Difficulties encountered when using standard DDRT-PCR include, a high incidence of false positives and redundant gene identification, poor reproducibility, biased gene display and lack of functional information about the cloned cDNA. The generation of false positives and redundancy can be highly problematic, resulting in an inordinate expenditure of resources to confirm appropriate differential expression and uniqueness of the isolated cDNAs. The cDNAs must be isolated from the gels in pure form (contamination of bands with multiple sequences complicates clone identification), reamplified, placed in an appropriate cloning vector, analyzed for authentic differential expression and finally sequenced. These limitations of the standard DDRT-PCR approaches emphasize the need for improvements in this procedure to more efficiently and selectively identify differentially expressed genes.

A number of modifications and improvements of the DDRT-PCR approach have been described (21-23). Single anchor or degenerate two-base anchor oligo dT primers can be used to streamline the massive numbers of reverse transcription and PCR reactions required for validation of cDNAs as well as to reduce false positives (24,25). Reproducibility can be improved by lengthening the arbitrary 5' primers to accommodate a convenient restriction site followed by two cycles of PCR with successive low- and high-stringency annealing temperatures (25,26). DDRT-PCR with inosine-containing 5' arbitrary primers can also increase reproducibility of this approach (27). However, since these modifications have only been analyzed using a subset of primers, further studies are necessary to validate these modifications of DDRT-PCR with additional primers and in several model systems.

In addition to genomic DNA contamination, mispriming, PCR artifacts, the high incidence of false positives and redundancy is also ascribed to poor separation between bands and the complexity of the templates amplified (28). Furthermore, poor separation can mask differentially expressed genes of low abundance under the intense signals generated by highly expressed genes. By enriching for unique cDNAs and removing common ones, it should in principle be possible to enrich for low abundant gene products and significantly decrease the complexity of amplified sequences. In addition, the sequence bias of DDRT-PCR should also be reduced by decreasing template complexity. These assumptions serve as the basis for the development of reciprocal subtraction differential RNA display (RSDD).

Subtractive hybridization, in which hybridization between tester and driver is followed by selective removal of common gene products, enriches for unique gene products in the tester cDNA population and reduces the abundance of common cDNAs (9). A subtracted cDNA library can be analyzed to identify and clone differentially expressed genes by randomly picking colonies or by differential screening (29-31). Although subtractive hybridization has been successfully used to clone a number of differentially expressed genes (5-7,10), this approach is both labor-intensive and does not result in isolation of the full spectrum of genes displaying altered expression (9,18).

In principle, DDRT-PCR performed with subtracted RNA or cDNA samples represents a powerful strategy to clone up and down-regulated gene products. This approach should result in the enrichment of unique sequences and a reduction or elimination of common sequences. This scheme should also result in a consistent reduction in band complexity on a display gel, thereby permitting a clearer separation of cDNAs resulting in fewer false positive reactions. Additionally, it should be possible to use fewer primer sets for reverse transcription and PCR reactions to analyze the complete spectrum of differentially expressed genes. Of particular importance for gene identification and isolation, rare gene products that are masked by strong common gene products should be displayed by using subtraction hybridization in combination with DDRT-PCR. In addition, the DDRT-PCR approach with subtractive libraries could also prove valuable for efficiently screening subtracted cDNA libraries for differentially expressed genes. However, even though subtraction hybridization plus DDRT-PCR appears attractive for the reasons indicated above, a previous attempt to use this approach has proven of only marginal success in consistently reducing the complexity of the signals generated, compared with the standard DDRT-PCR scheme (32).

We presently describe a reciprocal subtraction differential RNA display (RSDD) approach that efficiently and consistently reduces the complexity of DDRT-PCR and results in the identification and cloning of genes displaying anticipated differential expression.

SUMMARY OF THE INVENTION

This invention provides a method for identifying differentially expressed nucleic acids between two samples, comprising: (a) selecting a first and second nucleic acid sample, wherein the nucleic acid samples contain a repertoire of nucleic acids; (b) performing reciprocal subtraction between the nucleic acid samples to produce two subtracted nucleic acid samples; (c) amplifying the two subtracted nucleic acid samples; and (d) comparing the two subtracted nucleic acid samples to identify differentially expressed nucleic acids.

This invention also provides a method for identifying differentially expressed nucleic acids between two samples, comprising: (a) selecting a first and second nucleic acid sample, wherein the nucleic acid samples contain a repertoire of nucleic acids; (b) amplifying the two nucleic acid samples; (c) performing reciprocal subtraction between the amplified nucleic acid samples to produce two subtracted nucleic acid samples; and (d) comparing the two subtracted nucleic acid samples to identify differentially expressed nucleic acids.

This invention further provides the above-described methods, wherein the first and second nucleic acid samples are obtained from cells in different developmental stages.

This invention further provides the above-described methods, wherein the first and second nucleic acid samples are obtained from cells from different tissue types.

Also, this invention provides the above-described methods, wherein the 3' primer used in the PCR amplification is an oligo dT 3' primer.

In addition, this invention provides the above-described methods, wherein the 3' primer used in the PCR amplification is a single anchor oligo dT 3' primer.

This invention also provides the above-described methods, wherein the comparing of step (e) comprises using a gel to separate the nucleic acids from both of the libraries.

This invention provides the isolated nucleic acid identified by the the above-described methods, wherein the nucleic was not previously known to be differentially expressed between the two samples.

BRIEF DESCRIPTION OF THE FIGURES

FIG. 1 Identification of differentially expressed sequence tags using reciprocal subtraction differential RNA display (RSDD). Left panel: differential RNA display pattern of conventional DDRT-PCR with RNA from from E11 (C) and E11-NMT (T) cells and an RSDD analysis of reciprocally subtracted E11 minus E11-NMT (C/T) and E11-NMT minus E11 (T/C) cDNA libraries. Right panel: representative RSDD patterns using different sets of primers.

FIG. 2 Reverse Northern analysis of differentially expressed sequence tags identified by reciprocal subtraction differential RNA display (RSDD). Differentially expressed sequence tags obtained from RSDD were dot-blotted onto Nylon membranes and probed with 32P-cDNA reverse transcribed from RNA samples of E11 and E11-NMT cells.

FIG. 3A Differential expression of representative progression elevated genes (PEGen) and progression suppressed genes (PSGen) identified by reciprocal subtraction differential RNA display (RSDD) and reverse Northern blotting. Northern blots of E11 and E11-NMT RNA samples were probed with radiolabeled ($^{32}$P) expressed sequence tags identified by RSDD and reverse Northern blotting.

FIG. 5 cDNA fragment of PEGen 7—90% Homology to Human HPV16 E1BP. (Sequence ID No. 1)

FIG. 6 cDNA fragment of PEGen 8—Rat phosphofructose kinase C. (Sequence ID No. 2)

FIG. 7 First (Sequence ID No. 3) and second (Sequence ID No. 4) cDNA fragments of PEGen 13.

FIG. 8 cDNA fragment of PEGen 14. (Sequence ID No. 5)

FIG. 9 cDNA fragment of PEGen 15. (Sequence ID No. 6)

FIG. 10 cDNA fragment of PEGen 21 which has 94% homology to mouse FIN 14. (Sequence ID No. 7)

FIG. 11 cDNA fragment of PEGen 24. (Sequence ID No. 8)

FIG. 12 cDNA fragment of PEGen 26—Rat poly ADP-ribose polymerase. (Sequence ID No. 9)

FIG. 13 cDNA fragment of PEGen 28. (Sequence ID No. 10)

FIG. 14 cDNA fragment of PEGen 42. (Sequence ID No. 11)

FIG. 15 cDNA fragment of PEGen 43. (Sequence ID No. 12)

FIG. 16 cDNA fragment of PEGen 44. (Sequence ID No. 13)

FIG. 17 cDNA fragment of PEGen 48. (Sequence ID No. 14)

FIG. 18 cDNA fragment of PSGen 1 which has 80% homology to B. taurus supervillin. (Sequence ID No. 15)

FIG. 19 cDNA fragment of PSGen 2 which has 91% homology to human HTLV-1 Tax interacting protein. (Sequence ID No. 16)

FIG. 20 cDNA fragment of PSGen 4—Rat proteasome activator. (Sequence ID No. 17)

FIG. 21 cDNA fragment of PSGen 10—Rat Ferritin Heavy Chain. (Sequence ID No. 18)

FIG. 22 cDNA fragment of PSGen 12. (Sequence ID No. 19)

FIG. 23 cDNA fragment of PSGen 13. (Sequence ID No. 20)

FIG. 24 cDNA fragment of PSGen 23. (Sequence ID No. 21)

FIG. 25 cDNA fragment of PSGen 24. (Sequence ID No. 22)

FIG. 26 cDNA fragment of PSGen 25. (Sequence ID No. 23)

FIG. 27 cDNA fragment of PSGen 27. (Sequence ID No. 24)

DETAILED DESCRIPTION OF THE INVENTION

Figure 3B:
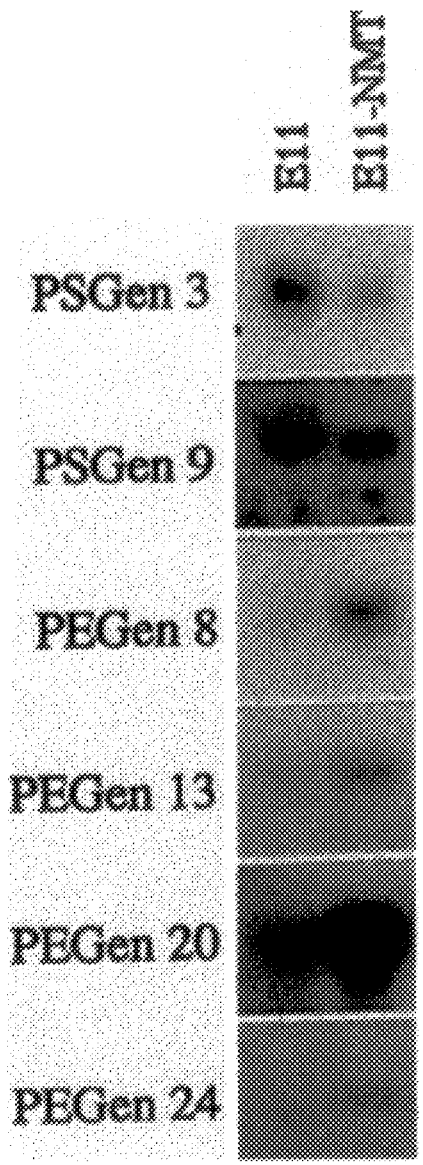
FIG. 3B Differential expression of representative progression elevated genes (PEGen) and progression suppressed genes (PSGen) identified by reciprocal subtraction differential RNA display (RSDD) and reverse Northern blotting.

This invention provides a method for identifying differentially expressed nucleic acids between two samples, comprising: (a) selecting a first and second nucleic acid sample, wherein the nucleic acid samples contain a repertoire of nucleic acids; (b) performing reciprocal subtraction between the nucleic acid samples to produce two subtracted nucleic acid samples; (c) amplifying the two subtracted nucleic acid samples; and (d) comparing the two subtracted nucleic acid samples to identify differentially expressed nucleic acids.

In an embodiment, the nucleic acid samples are mRNA or derived from mRNA. In another embodiment, the nucleic acid samples are total RNA. In another embodiment, the nucleic acid samples are cDNA. In another embodiment, the nucleic acid samples are a nucleic acid library.

In an embodiment, differentially expressed nucleic acids are expressed at different levels. In a further embodiment, one of the nucleic acids is not expressed. In a different embodiment, one of the nucleic acids is expressed in truncated form.

As used herein, reciprocal subtraction includes using nucleic acid sample A to subtract common nucleic acids from nucleic acid sample B (based on hybridization) and also using nucleic acid sample B to subtract common nucleic acids from nucleic sample A. In an embodiment, the complement of nucleic acid sample A is used to subtract nucleic acids from nucleic acid sample B and the complement of nucleic acid sample B is used to subtract nucleic acids from nucleic acid sample A. In a further embodiment, the RNA of nucleic acid sample A is used to subtract nucleic acids from nucleic acid sample B and the RNA of nucleic acid sample B is used to subtract nucleic acids from nucleic acid sample A. In yet another embodiment, the cDNA of nucleic acid sample A is used to subtract nucleic acids from nucleic acid sample B and the cDNA of nucleic acid sample B is used to subtract nucleic acids from nucleic acid sample A.

As used herein, methods of amplification include PCR and rolling circle replication.

A basic description of nucleic acid amplification is described in Mullis, U.S. Pat. No. 4,683,202, which is incorporated herein by reference. The amplification reaction uses a template nucleic acid contained in a sample, two primer sequences and inducing agents. The extension product of one primer when hybridized to the second primer becomes a template for the production of a complementary extension product and vice versa, and the process is repeated as often as is necessary to produce a detectable amount of the sequence.

The inducing agent may be any compound or system which will function to accomplish the synthesis of primer extension products, including enzymes. Suitable enzymes for this purpose include, for example, E.coli DNA polymerase I, thermostable Taq DNA polymerase, Klenow fragment of E.coli DNA polymerase I, T4 DNA polymerase, other available DNA polymerases, reverse transcriptase and other enzymes which will facilitate combination of the nucleotides in the proper manner to form amplification products. The oligonucleotide primers can be synthesized by automated instruments sold by a variety of manufacturers or can be commercially prepared based upon the nucleic acid sequence of this invention.

This invention also provides a method for identifying differentially expressed nucleic acids between two samples, comprising: a) selecting a first and second nucleic acid sample; b) producing libraries for the first and second nucleic acid sample; c) amplifying the two libraries; d) performing reciprocal subtraction between the amplified libraries to produce two subtracted libraries; and e) comparing the two subtracted libraries to identify differentially expressed nucleic acids.

This invention also provides a method for identifying differentially expressed nucleic acids between two samples, comprising: (a) selecting a first and second nucleic acid sample, wherein the nucleic acid samples contain a repertoire of nucleic acids; (b) amplifying the two nucleic acid samples; (c) performing reciprocal subtraction between the amplified nucleic acid samples to produce two subtracted nucleic acid samples; and (d) comparing the two subtracted nucleic acid samples to identify differentially expressed nucleic acids.

This invention also provides the above-described methods, wherein the two subtracted nucleic acid samples from step c are amplified prior to the comparing of step d.

This invention also provides the above-described methods, wherein the each of the nucleic acid samples comprises a library of nucleic acids.

This invention also provides the above-described methods, wherein the nucleic acid samples are obtained from total cellular RNA purified by hybridization with oligo (dT).

This invention also provides the above-described methods, wherein the nucleic acid samples are obtained from total RNA from E11 and E11-NMT cells.

E11 is an adenovirus-transformed rat embryo cell line that acquires an aggressive oncogenic progression phenotype when injected into athymic nude mice and reisolated in cell culture (E11-NMT).

This invention further provides the above-described methods, wherein the first and second nucleic acid samples are obtained from cells in different developmental stages.

This invention further provides the above-described methods, wherein the first and second nucleic acid samples are obtained from cells from different tissue types.

This invention further provides the above-described methods, wherein the first and second nucleic acid samples are obtained from cells that differ in their exposure to external factors or in their gene expression.

In an embodiment, cells that differ in their exposure to external factors or in their gene expression includes any cells that may have different levels of gene expression, wherein some genes may not be expressed at all. In another embodiment, cells that differ in their exposure to external factors or in their gene expression includes any cells that are likely to have different levels of gene expression, wherein some genes may not be expressed at all. In still another embodiment, cells that differ in their exposure to external factors or in their gene expression includes any cell that has a phenotypically recognizable difference.

A short list of examples of cells that differ in their exposure to external factors or in their gene expression includes: cancerous versus normal cells, advanced cancer progression cells versus ealier cancer stage cells, diseased cells versus nondiseased cells, infected cells versus noninfected cells, later developmental stage cells versus earlier developmental stage cells, cells after DNA damage versus cells before DNA damage, senescent cells versus younger cells, cells induced by growth factors versus cells not induced by growth factors, cells in the process of neurodegeneration versus normal cells, and cells exposed to a chemotherapeutic agent versus normal cells.

As used herein, different tissues types include but are not limited to tissues containing: cells grown under or exposed to different conditions, cells in different stages of development, cells treated with agents modifying cellular physiology, and cells having different functions.

In an embodiment, cells at different stages of development are cells taken or analyzed at times differing by one or more hours in the development of the cell or organism.

Further, this invention provides the above-described methods, wherein the amplifying of step (d) comprises PCR amplification.

Also, this invention provides the above-described methods, wherein the 3' primer used in the PCR amplification is an oligo dT 3' primer. A few examples of oligo dT primers are $T_{13}$, $T_{13}A$, and $T_{13}GA$.

In addition, this invention provides the above-described methods, wherein the 3' primer used in the PCR amplification is a single anchor oligo dT 3' primer. Olgio dT 3' primers include $T_{13}A$, $T_{13}C$, and $T_{13}G$.

This invention provides the above-described methods, wherein the PCR amplification uses a set of random primers.

This invention provides the above-described methods, wherein the 5' primer is an arbitrary primer.

This invention also provides the above-described methods, wherein the comparing of step (e) comprises using a gel to separate the nucleic acids from both of the substracted libraries.

In an embodiment, the gel is a polyacrylamide gel. In another embodiment, the gel is an agarose gel.

This invention further provides the above-described methods, further comprising PCR amplifying the first and second nucleic acid samples.

This invention also provides the above-described methods, further comprising reamplifying differentially expressed bands.

This invention also provides the above-described methods, further comprising reamplifying differentially expressed nucleic acid.

In one method of reamplifying differentially expressed bands, differentially amplified bands from plasmids of each subtracted library were marked with an 18G needle through the film and cut out with a razor. The cut out differentially expressed bands can be reamplified (i.e. by PCR) and examined by reverse Northern and Northern blot analyses.

In addition, this invention provides the above-described methods, wherein the comparing of step (e) comprises comparing the band intensities of the two amplified differentially expressed nucleic acids.

In addition, this invention provides the above-described methods, wherein the nucleic acid samples are mRNA or cDNA derived from mRNA.

In addition, this invention provides the above-described methods, wherein the comparing of step (e) comprises comparing the quantities of the two amplified differentially expressed nucleic acids.

This invention further provides the above-described methods, wherein the differences in band intensity between the two subtracted libraries are electronically quantified.

This invention further provides the above-described methods, wherein the differences in the quantities of nucleic acid between the two subtracted libraries are electronically quantified.

In one embodiment, electronic quantification involves using a scanner to detect the bands. In a further embodiment, computer software, such as Corel Draw, can be used to determine the pixel intensity of the scanned image, thereby quantifying the band intensity.

Also, this invention provides the above-described methods, wherein the libraries of step (b) are constructed with λ-ZAP cDNA library kits. One skilled in the art would recognize that any cDNA library would be suitable.

This invention provides the isolated nucleic acid identified by the the above-described methods, wherein the nucleic acid was not previously known.

This invention also provides the above-described isolated nucleic acid, wherein the isolated nucleic acid is the nucleic acid designated PSGen 12.

In addition, this invention provides the above-described isolated nucleic acid, wherein the isolated nucleic acid is the nucleic acid designated PSGen 13.

This invention provides the above-described isolated nucleic acid, wherein the isolated nucleic acid is the nucleic acid designated PSGen 23.

This invention provides the above-described isolated nucleic acid, wherein the isolated nucleic acid is the nucleic acid designated PSGen 24.

This invention provides the above-described isolated nucleic acid, wherein the isolated nucleic acid is the nucleic acid designated PSGen 25.

This invention also provides the above-described isolated nucleic acid, wherein the isolated nucleic acid is the nucleic acid designated PSGen 27.

This invention provides the above-described isolated nucleic acid, wherein the isolated nucleic acid is the nucleic acid designated PEGen 13.

This invention provides the above-described isolated nucleic acid, wherein the isolated nucleic acid is the nucleic acid designated PEGen 14.

This invention provides the above-described isolated nucleic acid, wherein the isolated nucleic acid is the nucleic acid designated PEGen 15.

This invention provides the above-described isolated nucleic acid, wherein the isolated nucleic acid is the nucleic acid designated PEGen 28.

This invention further provides the above-described isolated nucleic acid, wherein the isolated nucleic acid is the nucleic acid designated PEGen 24.

This invention provides the above-described isolated nucleic acid, wherein the isolated nucleic acid is the nucleic acid designated PEGen 42.

This invention provides the above-described isolated nucleic acid, wherein the isolated nucleic acid is the nucleic acid designated PEGen 43.

This invention provides the above-described isolated nucleic acid, wherein the isolated nucleic acid is the nucleic acid designated PEGen 44.

This invention provides the above-described isolated nucleic acid, wherein the isolated nucleic acid is the nucleic acid designated PEGen 48.

This invention will be better understood from the Experimental Details which follow. However, one skilled in the art will readily appreciate that the specific methods and results discussed are merely illustrative of the invention as described more fully in the claims which follow thereafter.

Experimental Details

We presently describe a reciprocal subtraction differential RNA display (RSDD) approach that efficiently and consistently reduces the complexity of DDRT-PCR and results in the identification and cloning of genes displaying anticipated differential expression. Proof of principle for the RSDD approach has come from its application for the identification of genes differentially expressed during cancer progression. RSDD has resulted in the identification and cloning of genes displaying elevated expression in progressed tumor cells (PEGen) and reduced expression in progressed tumor cells (PSGen). The model used for RSDD was an adenovirus-transformed rat embryo cell line, E11, that acquires an aggressive oncogenic progression phenotype when injected into athymic nude mice and reisolated in cell culture (E11-NMT) (10,33,34). Injection of E11 cells into nude mice results in tumors in 100% of animals with a tumor latency time of approximately 35 to 40 days, whereas E11-NMT cells form tumors in 100% of nude mice with a tumor latency time of 15 to 20 days (10,34,35). Additionally, E11 cells form colonies in agar with an efficiency of ~3%, whereas E11-NMT display an agar cloning efficiency of >30% (10,33,34). The increased tumorigenicity and enhanced anchorage independence phenotypes are key indicators of tumor progression in the E11/E11-NMT model system (10,33,34).

Differential RNA display was directly performed with reciprocally subtracted cDNA plasmid libraries (E11 minus E11-NMT and E11-NMT minus E11). Compared with the subtraction of PCR-amplified cDNA in Hakvoort et al., the subtracted cDNA libraries used in this experiment are free from potential PCR artifacts and provide more stable and consistent sources for DDRT-PCR analyzes. In addition, three single anchored oligo dT 3' primers were used instead of two-base-anchored approach described by Hakvoort et al (32). To further streamline the DDRT-PCR procedure, reamplified cDNAs identified using RSDD were analyzed using the reverse Northern blotting procedure (35,36). cDNAs displaying differential expression by reverse Northern blotting were subsequently confirmed for true differential expression by Northern analysis. These modifications incorporated in the RSDD strategy result in an efficient approach for using subtractive hybridization and DDRT-PCR for identifying differentially expressed genes.

Methods

Total RNA from E11 and E11-NMT cells was isolated by the guanidinium isothiocyanate/CsCl centrifugation procedure and poly $A^+$ RNA was purified with oligo(dT) cellulose chromatography (5). Two λ-ZAP cDNA libraries from E11 and E11-NMT mRNA's were constructed with λ-ZAP cDNA library Kits (Stratagene) following the manufacturer's protocol. Reciprocal subtraction between E11 and E11-NMT libraries was performed and two subtracted cDNA libraries (E11 minus E11-NMT and E11-NMT minus E11) were constructed as described previously. Bacterial plasmid libraries from the subtracted λ-ZAP cDNA libraries were obtained by in vivo excision following the manufacturer's protocol (Stratagene) and the plasmids were isolated with Qiagen columns (Qiagen Inc.).

The purified plasmids of reciprocally subtracted cDNA libraries were directly subjected to differential display as in Liang et. al. (38) with minor modifications. The plasmids of reciprocally subtracted cDNA libraries were PCR-amplified with the combination of three single-anchor 3' primers ($T_{13}A$, $T_{13}C$ or $T_{13}G$) and 18 arbitrary 5' 10-mer primers obtained from Operon Technology Inc. (Alameda, Calif. OPA 1-20 except OPA1 and 3). The 20 $\mu$l PCR reaction consisted of 10 mM Tris-HCl pH 8.4, 50 mM KCl, 1.5 mM $MgCl_2$, 2 $\mu$M each dNTP, 0.2 $\mu$M 5' arbitrary primer, 1 $\mu$M 3' anchor primer, 50 ng of plasmid of a subtracted library, 10 $\mu$Ci α-$^{35}$S-dATP (3000 Ci/mmole from Amersham) and 1 U of Taq DNA polymerase (Gibco BRL). The parameters of PCR were 30 sec at 95° C., 40 cycle of 30 sec at 95° C., 2 min. at 40° C. and 30 sec at 72° C. and additional 5 min. at 72° C. After the cycling, 10 $\mu$l of 95% formamide, 0.05% bromophenol blue and 0.05% xylene cyanol were added to each PCR reaction. The mixture was heated at 95° C. for 2 min and separated in a 5% denaturing DNA sequencing gel maintained at 50° C. PCR reactions of plasmids from each subtracted library in a primer set were run side by side. Differentially amplified bands from plasmids of each subtracted library were marked with an 18G needle through the film and cut out with a razor. The gel slice was put in 100 $\mu$l TE pH 8.0 and incubated at 4° C. overnight. After the incubation, the mixture was boiled for 5 min and microcentrifuged for two min. The supernatant was collected and stored at −20° C. until reamplification. The band extract was reamplified with the same cycling parameters in a 50 $\mu$l reaction consisting of 10 mM Tris-HCl pH 8.4, 50 mM KCl, 1.5 mM $MgCl_2$, 20 $\mu$M each dNTP, 0.2 $\mu$M 5' arbitrary primer, 1 $\mu$M 3' anchor primer, 5 $\mu$l of band extract and 2.5 U of Taq DNA polymerase (Gibco BRL).

Differential expression of the reamplified DNA fragment was scrutinized by reverse Northern and Northern blot analyses. In reverse Northern analysis, after confirmation in a 1% agarose gel, the reamplified DNA fragment (10 $\mu$l of PCR reaction) was mixed with 90 $\mu$l TE and spotted on a positively charged Nylon membrane (Boehringer Mannheim) with a 96-well vacuum manifold. The membrane was soaked with denaturing and neutralizing solution successively, and the spotted DNA was crosslinked to the membrane with a UV crosslinker (Stratagene). $^{32}$P-labeled first strand cDNA was prepared by reverse transcription of total RNA. After heating at 70° C. for 10 min and quenching on ice for two min, 0.4 $\mu$M each $T_{13}A$, $T_{13}G$ and $T_{13}C$ and 10 $\mu$g total RNA mixture was added with 50 mM Tris-HCl, pH 8.3, 75 mM KCl, 3 mM MgCl2, 10 mM DTT, 0.5 mM dATP, 0.5 mM dGTP, 0.5 mM dTTP, 0.02 mM dCTP, 0.5 $\mu$l RNase inhibitor (Gibco BRL), 100 $\mu$Ci dCTP (3000 Ci/mmole from Amersham) and 200 U Superscript RT II (Gibco BRL) in a final 25 $\mu$l reaction. The reaction mixture was incubated at 42° C. for one hr and at 37° C. for 30 min after addition of 2 $\mu$l of RNase H (10U, Gibco BRL). The membrane was hybridized at 42° C. overnight in a 50% formamide hybridization solution. The hybridized membrane was washed at room temperature for 15 min with 2× SSC containing 0.1% SDS twice and at 55° C. for at least one hr with 0.1× SSC containing 0.1% SDS, successively. The membrane was probed with the $^{32}$P-labeled cDNA of E11, stripped off and probed with $^{32}$P-labeled cDNA of E11-NMT. The signal intensity of each spot was normalized against that of GAPDH and compared between E11 and E11-NMT. Reamplified DNA fragments displaying differential expression levels ≧1.8-fold higher between the two cell types were selected and analyzed by Northern blotting analysis.

In Northern blot analysis, 10 μg of total RNA from E11 and E11-NMT cells were run side-by-side in a 1% agarose gel with formaldehyde and transferred to a positively charged Nylon membrane. Reamplification reaction (5 μl) was $^{32}$P-labeled with a multiprime labeling kit (Boehringer Mannheim) used to probe the membrane as described above. DNA fragments expressed differentially between E11 and E11-NMT in Northern blot analyses were cloned into the Eco RV site of the pZEro-2.1 cloning vector (Invitrogene) and sequenced. In order to confirm differential expression, the cloned cDNA fragment was released by Eco RI -Xho I, $^{32}$P-labeled and used to probe Northern blots as described above. Samples of RNAs from various E11 and E11-NMT derivatives displaying either a progressed or suppressed progression phenotype, based on nude mice tumorigenesis and soft agar cloning assays were analyzed. These included E11, E11-NMT, CREF X E11-NMT F1 and F2 somatic cell hybrids (suppressed progression phenotype), CREF X E11-NMT R1 and R2 somatic cell hybrids (progression phenotype), E11 X E11-NMT A6 somatic cell hybrid (suppressed progression phenotype), E11 X E11-NMT A6TD tumor-derived somatic cell hybrid (progression phenotype), E11 X E11-NMT 3b somatic cell hybrid (suppressed progression phenotype), E11 X E11-NMT 2a (progression phenotype), E11-NMT AZA B1 and C1 5-azacytidine treated E11-NMT clones (suppressed progression phenotype), E11-ras R12 clone containing the Ha-ras oncogene (progression phenotype) and E11-HPV E6/E7 clone containing the human papilloma virus-18 E6 and E7 gene region (progression phenotype). Differential expression of the PEGen and PSGen genes in the various cell types was confirmed using $^{32}$P-labeled probes and Northern hybridization analysis. After reconfirmation of differential expression, the plasmids containing the differentially expressed DNA fragments were sequenced by the dideoxy sequencing procedure.

Results and Discussion

Subtraction hybridization provides a direct means of enriching for unique cDNA species and eliminating common sequences between complex genomes. DDRT-PCR is a proven methodology for the rapid identification and cloning of differentially expressed sequences between cell types (3,4,22). In principle, subtraction hybridization combined with DDRT-PCR should reduce band complexity which often obscures the identification of differentially expressed genes and generates false positive signals (23,28). This strategy, RSDD, has been used to analyze genes differentially expressed during transformation progression. The differential RNA display pattern of E11 and E11-NMT cells using standard differential RNA display DDRT-PCR) and RSDD is shown in FIG. 1 (Left Panel). As predicted, the differential RNA display pattern of RSDD was much less complex than that of DDRT-PCR. The majority of bands common to both cDNA samples were eliminated using RSDD. These experiments demonstrate that subtractive hybridization prior to differential RNA display is effective in simplifying display patterns permits the efficient identification of differentially expressed cDNAs. Since RSDD significantly reduced the number of bands displayed, single anchor oligo dT primers, that can increase band numbers, were successfully used in subsequent applications of the RSDD approach (FIG. 1; Right Panel). Using RSDD, 235 differentially displayed cDNAs in the E11/E11-NMT tumor progression model system were isolated.

Hakvoort et. al. (32) used a reciprocal subtraction approach to analyze gene expression changes resulting during liver regeneration following 70% hepatectomy, i.e., normal liver subtracted from partially hepatectomized regenerating liver and vice versa. Although some bands displayed apparent enrichment, the complexity of the display pattern did not show appreciable simplification. These results are in stark contrast to RSDD, which results in a clear delineation and simplification of differentially expressed amplified bands (FIG. 1). Although conceptually similar, RSDD is significantly more effective than the subtraction plus DDRT-PCR approach described by Hakvoort et al. (32). The improved efficiency of RSDD versus the Hakvoort et al. (32) approach can be attributed to several factors. The approach of Hakvoort et al. (32) is based on the subtraction procedure described by Wang and Brown (38). This approach involves multiple rounds of PCR-amplification prior to each round of subtractive hybridization. In contrast, RSDD involves a single round of reciprocal subtraction that does not involve PCR amplification (5,10). In this respect, the complicated display pattern observed by Hakvoort et al. (32) even after three or four rounds of subtraction might result from reduced subtraction efficiency, PCR artifacts or a combination of these problems. Increasing the number of reactions by using two-base pair anchored oligo dT primers did not reduce the complexity of displayed bands (32). In these contexts, a critical component for the successful use of RSDD involves the use of an appropriate subtraction hybridization protocol, that can efficiently reduce cDNA complexity and generate stable populations of cDNAs for analysis.

Previous studies demonstrate that different gene cloning strategies, including DDRT-PCR, subtraction hybridization and electronic display, identify dissimilar differentially expressed genes (18). These results suggest that a single approach for gene identification may not identify the complete spectrum of differentially expressed genes (18). Similarly, RSDD and DDRT-PCR do not resolve the same differentially expressed bands (FIG. 1). Unique bands identified in DDRT-PCR that were differentially expressed when analyzed by Northern blotting were not the same as those found using RSDD and vise versa. These results are not surprising, since, as indicated above, subtraction hybridization and differential RNA display identified distinct differentially expressed genes. Apparently, specific differentially expressed genes are lost during subtraction hybridization and differential RNA display of subtracted cDNAs. On the basis of these considerations, it will be essential to use multiple gene discovery approaches to identify and clone the complete spectrum of differentially expressed genes.

DDRT-PCR can generate large numbers of differentially displayed bands making subsequent analysis both labor intensive and a daunting challenge. In order to reduce these limitations of DDRT-PCR, RSDD has been used in combination with reverse Northern analyses of isolated cDNAs. Gel extracted cDNA fragments were reamplified, dot-blotted on Nylon membranes and successively probed with reverse transcribed $^{32}$P-cDNA from E11 or E11-NMT RNAs (FIG. 2). Signals were detected in 181 reamplified bands out of 235 (77%). This number is lower than that observed using DDRT-PCR (51 out of 54). However, this comparison may not be accurate since only four arbitrary primers were used for DDRT-PCR and fewer differentially expressed bands were detected and isolated. A possible reason for the high incidence of false positives in RSDD may be due to the existence of foreign plasmid-like DNA in the cDNAs and the inaccurate reading properties of DDRT-PCR.

TABLE 1

Differentially Expressed cDNA Fragments Cloned by DDRT-PCR.

| Nomenclature | Identity | Homology |
|---|---|---|
| PEGen 41 | To be determined | |
| PEGen 42 | Novel | Novel |
| PEGen 43 | Novel | Novel |
| PEGen 44 | Novel | Novel |
| PEGen 45 | Hoxall locus antisense | mouse 90% |
| PEGen 46 | Glutamyl t-RNA synthetase | human 59% |
| PEGen 47 | To be determined | |
| PEGen 48 | Novel | Novel |
| PSGen 1 | Supervillin | *B. taurus* 80% |
| PSGen 2 | HTLV-1 Tax interacting protein | human 91% |
| PSGen 4 | Proteasome activator | Rat 100% |
| PSGen 19 | To be determined | |
| PSGen 26 | To be determined | |
| PSGen 27 | Novel | |

The signal intensities of the various cDNAs in reverse Northern analysis were quantified and normalized against that of GAPDH, which remained unchanged in E11 and E11-NMT cells. The PEG-3 (PEGen-3) gene (10) was used as an additional control, to verify increased expression in E11-NMT versus E11 cells. In the reverse Northern analyses, PEGen-3 levels were 4-fold higher in E11-NMT than in E11 cells, which coincided with Northern blotting results, thereby demonstrating the concordance of reverse Northern and Northern assays. A ≧1.8-fold differential cut-off (after normalization for GAPDH expression) was used to identify and isolate cDNA bands displaying modified expression in E11 versus E11-NMT cells. This resulted in the identification of 7 cDNAs with higher expression in E11 versus E11-NMT cells and 65 cDNAs with elevated expression in E11-NMT versus E11 cells. These results suggest that tumor progression in E11-NMT cells correlates with the increased expression of a large number of genes, whereas only a smaller subset of genes display decreased expression.

A problem present in DDRT-PCR, that is reduced but still can occur in RSDD, is the isolation of multiple cDNA species from what appears to be a single amplified band. When this occurs, these multiple species can produce spurious results when analyzed by reverse Northern analyses. For example, if two distinct species are isolated, one displaying modified expression and a second not displaying modified expression, an accurate estimate of differential expression will not be obtained by reverse Northern analysis. In this case, a number of potential false positives generated using reverse Northern analyses, may in reality not be false positives, but instead may represent multiple cDNAs. This problem may be ameliorated by performing single strand conformational polymorphism (SSCP) or reverse Northern analyses using cloned cDNA populations (39,40).

Figure 4:
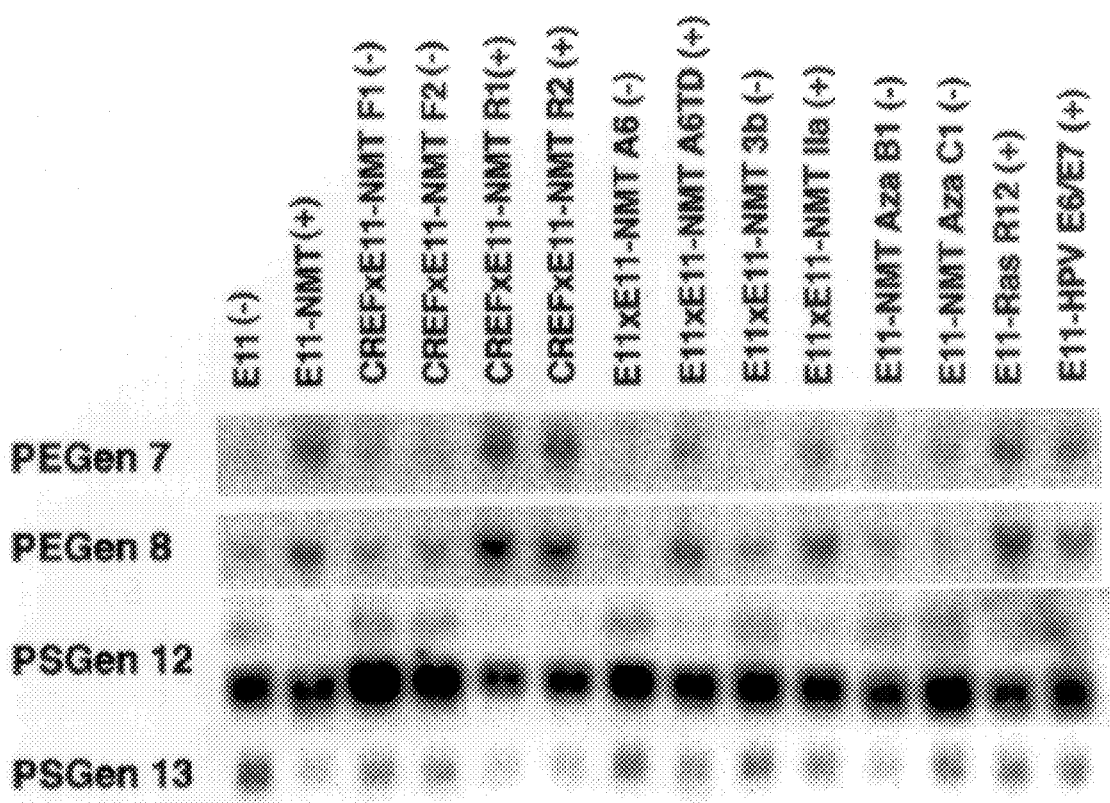
FIG. 4 Differential expression of representative progression elevated genes (PEGen) and progression suppressed genes (PSGen) identified by reciprocal subtraction differential RNA display (RSDD) and reverse Northern blotting. Northern blots of cells displaying various stages of transformation progression were probed with radiolabeled ($^{32}$P) expressed sequence tags identified by RSDD and reverse Northern blotting. The cell types used include, Unprogressed E11 (−), CREFxE11-NMT F1 (−) and CREFxE11-NMT F2 (−) somatic cell hybrids, E11xE11-NMT A6 (−) somatic cell hybrid, E11xE11-NMT 3b (−) somatic cell hybrid, and E11-NMT Aza B1 (−) and E11-NMT Aza C1 (−) 5-azacytidine treated E11-NMT clones; and Progressed E11-NMT (+), CREFxE11-NMT R1 (+) and CREFxE11-NMT R2 (+) somatic cell hybrids, E11xE11-NMT A6TD (+) nude mouse tumor derived somatic cell hybrid, E11xE11-NMT IIa (+) E11-Ras R12 (+) a Ha-ras transformed E11 clone and E11-HPV E6/E7 (+) an E11 clone transformed by the E6 and E7 region of HPV-18.

The expression pattern of representative RSDD-derived cDNAs in E11 versus E11-NMT and in a more expanded E11/E11-NMT progression cell culture series is shown in FIGS. 3 and 4, respectively. Reverse Northern results correlated well with Northern blots using E11 and E11-NMT (~80% concordance) or a larger panel of cells differentially displaying the progression phenotype, including progression negative, E11, CREF x E11-NMT F1, CREF X E11-NMT F2, E11 X E11-NMT A6, E11 X E11-NMT 3b, E11-NMT Aza B1 and E11-NMT Aza C1, and progression positive E11-NMT, CREF X E11-NMT R1, CREF X E11-NMT R2, E11 X E11-NMT A6TD, E11 X E11-NMT IIa, E11-ras and E11-HPV E6/E7. Sequence analysis of the various progression upregulated genes (PEGen) and progression suppressed genes (PSGen) identified both known and unknown genes (Table 2). Known PEGen genes included PEGen 7 (HPV16 E1BP), PEGen 8 (PFK-C), PEGen 21 (FIN 14) and PEGen 26 (poly ADP-ribose polymerase) and a known PSGen gene was PSGen 10 (ferritin heavy chain). Two PEGen genes out of six were found to be novel (PEGen 14 and PEGen 24) and two PSGen genes out of three were found to be novel (PSGen 12 and PSGen 13) (Table 2).

TABLE 2

Differentially Expressed cDNA Fragments Cloned by RSDD

| Nomenclature | Identity | Homology |
|---|---|---|
| PEGen 4 | To be determined | |
| PEGen 7 | HPV16 E1BP | Human 90% |
| PEGen 8 | PFK-C | Rat 100% |
| PEGen 13 | Novel | Novel |
| PEGen 14 | Novel | Novel |
| PEGen 15 | Novel | Novel |
| PEGen 21 | FIN 14 | Mouse 94% |
| PEGen 22 | To be determined | |
| PEGen 23 | To be determined | |
| PEGen 24 | Novel | Novel |
| PEGen 25 | To be determined | |
| PEGen 26 | Poly ADP-ribose Polymerase | Rat 100% |
| PEGen 27 | To be determined | |
| PEGen 28 | Novel | Novel |
| PEGen 29 | To be determined | |
| PEGen 30 | To be determined | |
| PEGen 31 | To be determined | |
| PEGen 33 | To be determined | |
| PEGen 34 | To be determined | |
| PEGen 35 | To be determined | |
| PEGen 36 | To be determined | |
| PEGen 37 | To be determined | |
| PEGen 38 | To be determined | |
| PEGen 39 | To be determined | |
| PEGen 40 | To be determined | |
| PEGen 49 | To be determined | |
| PEGen 50 | To be determined | |
| PEGen 51 | To be determined | |
| PEGen 52 | To be determined | |
| PSGen 7 | To be determined | |
| PSGen 8 | To be determined | |
| PSGen 9 | To be determined | |
| PSGen 10 | Ferritin Heavy Chain | Rat 100% |
| PSGen 11 | To be determined | |
| PSGen 12 | Novel | Novel |
| PSGen 13 | Novel | Novel |
| PSGen 14 | To be determined | |
| PSGen 15 | To be determined | |
| PSGen 16 | To be determined | |
| PSGen 17 | To be determined | |
| PSGen 18 | TO be determined | |
| PSGen 20 | To be determined | |
| PSGen 21 | To be determined | |
| PSGen 22 | To be determined | |
| PSGen 23 | Novel | Novel |
| PSGen 24 | Novel | Novel |
| PSGen 25 | Novel | Novel |

PEGen 7 is expressed at ~5-fold higher levels in E11-NMT than in E11 cells. PEGen 7 is ~90% homologous to 16E1-BP, a cDNA encoding a protein identified using the yeast two-hybrid assay that interacts with human papillomavirus type 16 E1 protein (41). 16E1-BP encodes a 432aa protein of unknown function but does contain an ATPase signature motif (Gly-$X_4$-Gly consensus ATP binding motif at aa 179 through 186). 16E1-BP appears to be a form of TRIP13, a protein previously shown to bind thyroid hormone receptor in yeast two-hybrid assays. The role of PEGen 7/16E1-BP in the progression phenotype in the E11/E11-NMT progression model is not known. Additional studies are necessary to determine if this gene change is associative or causative of transformation progression.

PEGen 8 is expressed at ~3- to 4- fold higher levels in E11-NMT than in E11 cells. PEGen 8 shows 100% homology to rat phosphofructokinase C (PFK-C) (42). PFK catalyzes the rate-limiting and committed step in glycolysis, the conversion of fructose 6-phosphate to fructose 1,6-biphosphate. Three subunit isozymes of PFK have been identified, that form homo- and heterotetramers with differing catalytic and allosteric properties. PFK-M is specific for cardiac and skeletal muscle, PFK-L is expressed in many tissues but is most abundant in the liver and PFK-C is expressed in several brain regions and the anterior pituitary but not in liver, skeletal muscle, or several other human tissues. The cDNA of PFK-C isolated from a rat hypothalamic cDNA library is 2643 bp and encodes a protein of 765aa (42). In a recent study, Sanchez-Martinez and Aragon (43) demonstrated that PFK-C is the predominant form of PFK in ascites tumor cells (obtained from a transplantable mouse carcinoma of mammary origin), whereas PFK-L is most abundant in the normal mammary gland. These results suggest the interesting possibility that PFK-C might contribute to the malignant nature of specific target cells. The role of PEGen 8/PFK-C in progression in the E11/E11-NMT model remains to he determined.

PEGen 21 is expressed at ~3- to 4-fold higher levels in E11-NMT than in E11 cells. PEGen 21 displays ~94% homology with the fibroblast growth factor-4 inducible gene FIN-14 (44). FIN-14 is a novel cDNA of unknown function that hybridizes with a 4.5 kb mRNA that is induced 4-fold in NIH3T3 mouse cells following treatment with FGF-4. The induction of FIN-14 occurs late (18 hr) after treatment with FGF-4 and does not occur when cells are treated for 18 hr with FGF-4 in the presence of cycloheximide (44). These results confirm that FIN-14 encodes a late-inducible gene. Moreover, nuclear run-on assays document that FIN-14 is trancriptionally activated in NIH3T3 cells following growth factor stimulation. Tissue distribution studies indicate expression of a single mRNA species in the kidney with low levels of expression observed in several other tissues including testis and thymus. Mouse embryogenesis studies indicate that FIN-14 expression occurs constitutively in mouse embryos between day 10.5 and 15.5. Unlike NIH3T3, FIN-14 was constitutively expressed in PC12 cells and its level did not vary appreciably in response to growth factor stimulation. The role of PEGen 21/FIN-14 in progression in E11/E11-NMT model system is not currently known.

The PSGen cDNAs, PSGen-12 and PSGen-13, consist of sequences without homology to those presently reported in various DNA databases. Expression of these cDNAs is ~3- to 4-fold higher in E11 versus E11-NMT cells (FIG. 3). It is not currently known whether these genes simply correlate with or functionally regulate the progression phenotype. The identification of full-length cDNAs for PSGen-12 and PSGen-13 are in progress and once identified experiments can be conducted to directly define the role of these PSGen's in cancer progression.

We presently demonstrate that a modified differential RNA display technique, RSDD, can efficiently identify differentially expressed cDNAs. As predicted, subtractive hybridization prior to differential RNA display greatly reduces band complexity, a problem encountered in standard DDRT-PCR in which RNA samples are directly analyzed without subtraction. Unlike a previous report using subtracted cDNAs processed through successive rounds of PCR (32,45), common bands were eliminated using reciprocally subtracted cDNA libraries that had not been processed using PCR. In addition to subtraction hybridization, the discovery of differentially expressed genes was further streamlined by using reverse Northern analyses with isolated cDNAs. With 3 single anchored oligo dT primers and 18 arbitrary 5' primers, 72 bands were identified that displayed differential expression using reverse Northern analysis. Currently, 40 of these cDNA species have been analyzed by Northern blotting and found to display differential expression in E11 versus E11-NMT cells. Subsequent studies with the majority of these RSDD cDNAs demonstrated coordinated expression with the progression phenotype in a large panel of unprogressed and progressed transformed cells. Current sequence analysis of the cloned cDNA fragments revealed 9 different genes, including 4 novel genes not reported in recent DNA databases. RSDD represents a method of choice either as a more efficient and less time consuming modification of the differential RNA display strategy or as a screening methodology for identifying differentially expressed genes in reciprocally subtracted cDNA libraries.

REFERENCES

1. Fisher, P. B. (Ed.) Mechanisms of Differentiation: Model Cell Culture Systems for Studying Differentiation. Vol. 1, pp. 1–164. Boca Raton, Fla.: CRC Press, Inc., 1990.
2. Fisher, P. B. (Ed.) Mechanisms of Differentiation: Modulation of Differentiation by Exogenous Agents. Vol. 2, pp. 1–205. Boca Raton, Fla.: CRC Press, Inc., 1990.
3. Watson, J. B. and Margulies, J. E. Differential cDNA screening strategies to identify novel stage-specific proteins in the developing mammalian brain. Developmental Neuroscience 15: 77–86, 1993.
4. Winkles, J. A. Serum- and polypeptide growth factor-inducible gene expression in mouse fibroblasts, Prog. Nucl. Acid Res. & Mol. Biol. 58: 41–78, 1998.
5. Jiang, H. and Fisher, P. B. Use of a sensitive and efficient subtraction hybridization protocol for the identification of genes differentially regulated during the induction of differentiation in human melanoma cells. Mol. Cell. Different. 1: 285–299, 1993.
6. Jiang, H., Lin, J. J., Su, Z. Z., Goldstein, N. I., and Fisher, P. B. Subtraction hybridization identifies a novel melanoma differentiation associated gene, mda 7, modulated during human melanoma differentiation, growth and progression. Oncogene 11: 2477–2486, 1995.
7. Jiang, H., Lin, J., Su, Z. Z., Herlyn, M., Kerbel, R. S., Weissman, B. E., Welch, D. R., and Fisher, P. B. The melanoma differentiation -associated gene melanoma cells. Oncogene 10. 1855–1864, 1995.
8. Jiang, H., Su, Z. Z., Lin, J. J., Goldstein, N. I., Young, C. S., and Fisher, P. B. The melanoma differentiation associated gene mda-7 suppresses cancer cell growth. Proc. Natl. Acad. Sci. USA 93. 9160–9165, 1996.
9. Sagerstrom, C. G., Sun, B. I., and Sive, H. L. Subtractive cloning: past, present, and future. Annu. Rev. Biochem. 66. 751–783,1997.
10. Su, Z.-z., Shi, Y., and Fisher, P. B. Subtraction hybridization identifies a transformation progression-associated gene PEG-3 with sequence homology to a growth arrest and DNA damage-inducible gene, Proc. Natl. Acad. Sci. USA 94:9125–9130, 1997.
11. Liang, P. and Pardee, A. B. Differential display of eukaryotic messenger RNA by means of the polymerase chain reaction. Science 257. 967–971, 1992.
12. Shen, R., Su, Z. Z., Olsson, C. A., and Fisher, P. B. Identification of the human prostatic carcinoma oncogene PTI-1 by rapid expression cloning and differential RNA display. Proc. Natl. Acad. Sci. USA 92:6778–6782, 1995.

13. Ralph, D., McClelland, M., and Welsh, J. RNA fingerprinting using arbitrarily primed PCR identifies differentially regulated RNAs in mink lung (Mv1 Lu) cells growth arrested by transforming growth factor beta 1. Proc. Nat. Acad. Sci. USA 90:10710–10714, 1993.
14. McClelland, M. and Welsh, J. RNA fingerprinting by arbitrarily primed PCR, PCR Methods & Applications 4: S66–81, 1994.
15. Hubank, M. and Schatz, D. G. Identifying differences in mRNA expression by representational difference analysis of cDNA. Nucl. Acids Res. 22: 5640–5648, 1994.
16. Velculescu, V. E., Zhang, L., Vogelstein, B., and Kinzler, K. W. Serial-analysis of gene expression. Science 270. 484–487, 1995.
17. Zhang, L., Zhou, W., Velculescu, V. E., Kern, S. E., Hruban, R. H., Hamilton, S. R., Vogelstein, B., and Kinzler, K. W. Gene expression profiles in normal and cancer cells. Science 276:1268–1272, 1997.
18. Wan, J. S., Sharp, S. J., Poirier, G. M.-C., Wagaman, P. C., Chambers, J., Pyati, J., Hom, Y.-L, Galindo, J. E., Huvar, A., Peterson, P. A., Jackson, M. R., and Erlander, M. G. Cloning differentially expressed mRNAs. Nature Biotechnology 14:1685–1691, 1996.
19. Adams, M. D., Kerlavage, A. R., Fields, C., and Venter, J. C. 3,400 new expressed sequence tags identify diversity of transcripts in human brain. Nature Genetics 4: 256–267, 1993.
20. Schena, M., Shalon, D., Davis, R. W., and Brown, P. O. Quantitative monitoring of gene expression patterns with a complementary DNA microarray. Science 270: 467–470, 1995.
21. Liang, P. and Pardee, A. B. Differential display. A general protocol. Meth. Mol. Biol. 85. 3–11, 1997.
22. Liang, P. and Pardee, A. B. Recent advances in differential display. Curr. Opinion Immunol. 7. 274–280, 1995.
23. Debouck, C. Differential display or differential dismay. Curr. Opinion Biotechnology 6: 597–599, 1995.
24. Liang, P., Averboukh, L., and Pardee, A. B. Distribution and cloning of eukaryotic mRNAs by means of differential display: refinements and optimization. Nucl. Acids Res. 21: 3269–3275, 1993.
25. Liang, P., Zhu, W., Zhang, X., Guo, Z., O'Connell, R. P., Averboukh; L, Wang, F., and Pardee, A. B. Differential display using one-base anchored oligo dT primers. Nucl. Acids Res. 22:5763–5764, 1994.
26. Zhao, S., Ooi, S. L., and Pardee, A. B. New primer strategy improves precision of differential display. Biotechniques 18: 842–846, 848, 850, 1995.
27. Rohrwild, M., Alpan, R. S., Liang, P., and Pardee, A. B. Inosine-containing primers for mRNA differential display. Trends in Genetics 11: 300, 1995.
28. Averboukh, L., Douglas, S. A., Zhao, S., Lowe, K., Maher, J., and Pardee, A. B. Better gel resolution and longer cDNAs increase the precision of differential display. Biotechniques 20: 918–921, 1996.
29. Rangnekar, V. V., Waheed, S., and Rangnekar, V. M. Interleukin-1 inducible tumor growth arrest is characterized by activation of cell type-specific Hearlyn gene expression programs. J. Biol. Chem. 267: 6240–6248, 1992.
30. Maser, R. L. and Calvet, J. P. Analysis of differential gene expression in the kidney by differential cDNA screening, subtractive cloning, and mRNA differential display. Seminars in Nephrology 15. 29–42, 1995.
31. Wong, B., Park, C. G., and Choi, Y. Identifying the molecular control of T-cell death; on the hunt for killer genes. Semin. Immunol. 9: 7–16, 1997.
32. Hakvoort, T.B., Leegwater, A. C., Michiels, F. A., Chamuleau, R. A., and Lamers, W. H. Identification of enriched sequences from a cDNA subtraction-hybridization procedure. Nucl. Acids Res. 22: 878–879, 1994.
33. Babiss, L. E., Zimmer, S. G., and Fisher, P. B. Reversibility of progression of the transformed phenotype in Ad5-transformed rat embryo cells. Science 228. 1099–1101, 1985.
34. Reddy, P. G., Su, Z.-z., and Fisher, P. B. Identification and cloning of genes involved in progression of transformed phenotype. In: K. W. Adolph (ed.) In: Chromosome and Genetic Analysis, Methods in Molecular Genetics, Vol. 1, pp. 68–102. Orlando, Fla.: Academic Press, Inc., 1993.
35. Zhang, H., Zhang, R., and Liang, P. Differential screening of differential display cDNA products by reverse northern. Meth. Mol. Biol. 85- 87–93, 1997.
36. Zhao, S., Ooi, S. L., Yang, F. C., and Pardee, A. B. Three methods for identification of true positive cloned cDNA fragment in differential display. Biotechniques 20: 400–404, 1996.
37. Liang, P., Bauer, D., Averboukh, L., Warthoe, P., Rohrwild, M., Muller, H., Strauss, M., and Pardee, A. B. Analysis of altered gene expression by differential display. Meth. Enzymol. 254:304–321, 1995.
38. Wang, Z. and Brown, D. D. A gene expression screen. Proc. Natl. Acad. Sci. USA 88. 11505–11509, 1991.
39. Zhang, H., Zhang, R., and Liang, P. Differential screening of gene expression difference enriched by differential display. Nucl, Acids Res. 24: 2454–2455, 1996.
40. Mathieu-Daude, F., Cheng, R., Welsh, J., and McClelland, M. Screening of differentially amplified cDNA products from RNA arbitrarily primed PCR fingerprints using single strand conformation polymorphism (SSCP) gels. Nucl. Acids Res. 24: 1504–1507, 1996.
41. Yasugi, T., Vidal, M., Saka, H., Howley, P. M., and Benson, J. D. Two classes of human papillomavirus type 16 E1 mutants suggest pleiotropic conformational constraints affecting E1 multimerization, E2 interaction, and interaction with cellular proteins. J. Virol. 71: 5941–5951, 1997.
42. Gekakis, N., Johnson, R. C., Jerkins, A., Mains, R. E., and Sul, H. S. Structure, distribution, and functional expression of the phosphofructokinase C isozyme. J. Biol. Chem. 269. 3348–3355, 1994.
43. Sanchez-Martinez, C. and Aragon, J. J. Analysis of phosphofructokinase subunits and isozymes in ascites tumor cells and its original tissue, murine mammary gland. FEBS Letters 409. 86–90, 1997.
44. Guthridge, M. A., Seldin, M., and Basilico, C. Induction of expression of growth-related genes by FGF-4 in mouse fibroblasts. Oncogene 12:1267–1278, 1997.
45. Wu, C. G., Hakvoort, T. B., Lamer s, W. H., and Chamuleau, R. A. Isolation of up- and down-regulated cDNAs associated with hepatocellular carcinoma by a subtraction-enhanced display technique. Biochim. Biophys. Acta. 1315. 169–175, 1996.

What is claimed is:

1. A method for identifying differentially expressed nucleic acids between two samples, comprising:
   a. selecting a first and second nucleic acid sample, wherein the nucleic acid samples contain a repertoire of nucleic acids;
   b. performing reciprocal subtraction between the nucleic acid samples to produce two subtracted nucleic acid samples;
   c. amplifying the two subtracted nucleic acid samples; and
   d. comparing the two subtracted nucleic acid samples to identify differentially expressed nucleic acids.

2. A method for identifying differentially expressed nucleic acids between two samples, comprising:
   a. selecting a first and second nucleic acid sample, wherein the nucleic acid samples contain a repertoire of nucleic acids;
   b. amplifying the two nucleic acid samples;
   c. performing reciprocal subtraction between the amplified nucleic acid samples to produce two subtracted nucleic acid samples; and
   d. comparing the two subtracted nucleic acid samples to identify differentially expressed nucleic acids.

3. The method of claim 2, wherein the two subtracted nucleic acid samples from step c are amplified prior to the comparing of step d.

4. The method of claim 1 or 2, wherein the each of the nucleic acid samples comprises a library of nucleic acids.

5. The method of claim 1 or 2, wherein the nucleic acid samples are mRNA or cDNA derived from mRNA.

6. The method of claim 1 or 2, wherein the nucleic acid samples are obtained from total RNA from E11 and E11-NMT cells.

7. The method of claim 1 or 2, wherein the first and second nucleic acid samples are obtained from cells that differ in their exposure to external factors or in their gene expression.

8. The method of claim 1 or 2, wherein the first and second nucleic acid samples are obtained from cells in different developmental stages.

9. The method of claim 1 or 2, wherein the amplifying of step (d) comprises PCR amplification.

10. The method of claim 9, wherein the PCR amplification uses a set of random primers.

11. The method of claim 9, wherein the 3' primer used in the PCR amplification is a single anchor oligo dT 3' primer.

12. The method of claim 9, wherein the 5' primer is an arbitrary primer.

13. The method of claim 1 or 2, wherein the comparing of step (e) comprises using a gel to separate the nucleic acids from both of the libraries.

14. The method of claim 1 or 2, further comprising PCR amplifying the first and second nucleic acid samples.

15. The method of claim 1 or 2, further comprising reamplifying differentially expressed nucleic acids.

16. The method of claim 1 or 2, wherein the comparing of step (e) comprises comparing the quantities of the two amplified differentially expressed nucleic acids.

17. The method of claim 1 or 2, wherein differences in the quantities of nucleic acid between the two subtracted libraries are electronically quantified.

18. The method of claim 1 or 2, wherein the libraries of step (b) are constructed with λ-ZAP cDNA library kits.

* * * * *

UNITED STATES PATENT AND TRADEMARK OFFICE
CERTIFICATE OF CORRECTION

PATENT NO. : 5,882,874
DATED : March 16, 1999
INVENTOR(S) : Paul B. Fisher

It is certified that error appears in the above-indentified patent and that said Letters Patent is hereby corrected as shown below:

column 1, line 3 please insert--The invention disclosed herein was made with Government support under NIH Grant No. CA35675. Accordingly, the U.S. Government has certain rights in this invention.-- column 7, line 42 "substracted" should read --subtracted-- column 9, line 43 "analyzes" should read --analysis-- coulumn 15, line 25 "he" should read --be--

Signed and Sealed this

Twenty-third Day of January, 2001

Attest:

Q. TODD DICKINSON

*Attesting Officer*  *Commissioner of Patents and Trademarks*

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 371 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:1:

```
TAAANCGGTG GTACTGCTGC ACGTCCTCC  GGGTACTGGA AAGACATCCC TTTGTAAGGC      60
ATTAGCCCAG AAACTGACCA TCAGACTGTC AANCAGGTAC CGGTATGGCC AGTTAATTGA     120
AATAAACAGC CACAGCCTAT TTTCTAAGTG GTNTTCAGAA AGTGGCAAGT TGGTAACTAA     180
GATGTTCCAG AAGATTCANG ACTTGATTGA TGATAANNAA NCTTTGGTGT TTGTCCTGAT     240
TGATGANGTA AGCACTCANN GGTACTCATT CTTNGTCTGC ATTGCCTCTT GCTATTACTG     300
CCTGATCCCT CTCATTTGGT TCACTGTGTC GCNANCTCTT TTCTATGGAT CTTTTCCNAN     360
CCACCCGTTT C                                                           371
```

( 2 ) INFORMATION FOR SEQ ID NO:2:

( i ) SEQUENCE CHARACTERISTICS:
        ( A ) LENGTH: 245 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:2:

```
GTGACGTAGG GTCTGTTGCG TCAATGGTTA TAGCAAGTGA TGCTCTCTGA TTATTACTGC      60
TGACAATACT CGGCCAACAA TTCTTGCATA GAGTGCTGAT AAATAACTAT GTTACAAAAA     120
GGGGTGGTCC CTGGAGAACA TTACAGGCTT CCCTAGGTAA GTGTGCAGGT CAGGAGACGG     180
CATATTCAAT CAGATGGCTG ATAGTTCTCC GTGGTTATGC ACCGGCTCCA GCTTGCCTAC     240
GTCAC                                                                  245
```

( 2 ) INFORMATION FOR SEQ ID NO:3:

( i ) SEQUENCE CHARACTERISTICS:
        ( A ) LENGTH: 178 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:3:

```
GCAGCATGAT GAATTTAATG CAACAGTCAT AGCAGGGCAA GGGGAGAGAA AGGCAGATGG      60
ACTATCTGCA TCATCAAGCG AGGGCTTGTG TCGGCGGCTA TGTGCAGAGA CGAGCAGGGC     120
GAGGCACTTA AAAGCTGCTN GATGAAAATC CACCCAGGAG AANTCTGGGC CTACGTCA      178
```

( 2 ) INFORMATION FOR SEQ ID NO:4:

( i ) SEQUENCE CHARACTERISTICS:

(A) LENGTH: 191 base pairs
(B) TYPE: nucleic acid
(C) STRANDEDNESS: Not Relevant
(D) TOPOLOGY: linear (ii) MOLECULE TYPE: cDNA (xi) SEQUENCE DESCRIPTION: SEQ ID NO:4:

| | | | | | |
|---|---|---|---|---|---|
| TGACGTAGGC | CCAGACTTCT | CCTGGGTGGA | TTTTCATCCA | GCAGCTTTTA | AGTGCCTCGC | 60
| CCTGCTCGTC | TCTGCACATA | GCCGCCGACA | CAAGCCCTCG | CTTGATGATG | CAGATAGTCC | 120
| ATCTGCCTTT | CTCTCCCCTT | GCCCTGCTAT | GACTGTTGCA | TTAAATTCAT | CATGCTGCCA | 180
| AAAAAAAAA | A | | | | | 191

(2) INFORMATION FOR SEQ ID NO:5:

(i) SEQUENCE CHARACTERISTICS:
(A) LENGTH: 124 base pairs
(B) TYPE: nucleic acid
(C) STRANDEDNESS: Not Relevant
(D) TOPOLOGY: linear (ii) MOLECULE TYPE: cDNA (xi) SEQUENCE DESCRIPTION: SEQ ID NO:5:

| | | | | | |
|---|---|---|---|---|---|
| GCCATAAATA | CACTTTATTT | CATTCGAAAT | GCATAATCAC | ACTGGGAGCA | CTCCCTTTGG | 60
| AGCACTCCTC | TAGCAGCAGG | TCCGAAGTGC | TCCAGCATCG | TCAGCTGGCT | CCAACACCTA | 120
| CGTC | | | | | | 124

(2) INFORMATION FOR SEQ ID NO:6:

(i) SEQUENCE CHARACTERISTICS:
(A) LENGTH: 61 base pairs
(B) TYPE: nucleic acid
(C) STRANDEDNESS: Not Relevant
(D) TOPOLOGY: linear (ii) MOLECULE TYPE: cDNA (xi) SEQUENCE DESCRIPTION: SEQ ID NO:6:

| | | | | | |
|---|---|---|---|---|---|
| TTTTTTTTT | TTTGGAAACA | GAATAAAGTG | CTTTATTCTC | TGGCTGGCTC | TCCTACGTCA | 60
| C | | | | | | 61

(2) INFORMATION FOR SEQ ID NO:7:

(i) SEQUENCE CHARACTERISTICS:
(A) LENGTH: 216 base pairs
(B) TYPE: nucleic acid
(C) STRANDEDNESS: Not Relevant
(D) TOPOLOGY: linear (ii) MOLECULE TYPE: cDNA (xi) SEQUENCE DESCRIPTION: SEQ ID NO:7:

| | | | | | |
|---|---|---|---|---|---|
| TCGGCGATAG | CATTGGAGCA | AGTCTTATCA | GCAAGCAATG | TTTTCAGTTA | TGTTTCAAAG | 60
| TTAAGAATGG | GTTTAAACTT | GCTGAACGTA | AAGATTGACC | CTCAAGTCAC | TGTAGCTTTA | 120
| GTACTTGCTT | ATTGTATTAG | TTTANATGCT | AGCACCGCAT | GTGCTCTGCA | TATTCTGGTT | 180
| TTATTAAAAT | AAAAAGTTGA | ACTGCAAAAA | AAAAAA | | | 216

(2) INFORMATION FOR SEQ ID NO:8:

(i) SEQUENCE CHARACTERISTICS:
(A) LENGTH: 334 base pairs
(B) TYPE: nucleic acid ( C ) STRANDEDNESS: Not Relevant
( D ) TOPOLOGY: linear ( i i ) MOLECULE TYPE: cDNA ( x i ) SEQUENCE DESCRIPTION: SEQ ID NO:8:

| | | | | | | |
|---|---|---|---|---|---|---|
| TTTTTTTTT | TTTTTTTTT | TTTTTTTTT | TTTTTTTTT | TNGCCAGGCT | ATGTCTCAGA | 6 0 |
| CTTTATTATT | ATTATTATTA | TTATTATTAT | TATAAATAAA | ACATGTNCTT | TCAATTAGGT | 1 2 0 |
| TACAANAGTA | TTTATCTCCA | TAACGCTTCT | TCATACATCC | TTAGTTTTGG | ATTAAAGTAC | 1 8 0 |
| CATCCACCCC | AACTCAAACT | GTAACCCCCA | GTAATCCCCT | CTAACGTGGA | AATTTCTGGT | 2 4 0 |
| TTAACAACTC | AGTTAACTGC | CCCACAAACA | GTGGGAGGCC | GCTCTTGCAT | GGCTATGCCA | 3 0 0 |
| CGTAACCCTT | CACTGCTTCA | CTTCTTCGCT | GGCT | | | 3 3 4 |

( 2 ) INFORMATION FOR SEQ ID NO:9:

( i ) SEQUENCE CHARACTERISTICS:
( A ) LENGTH: 136 base pairs
( B ) TYPE: nucleic acid
( C ) STRANDEDNESS: Not Relevant
( D ) TOPOLOGY: linear ( i i ) MOLECULE TYPE: cDNA ( x i ) SEQUENCE DESCRIPTION: SEQ ID NO:9:

| | | | | | | |
|---|---|---|---|---|---|---|
| GACCGCTTGT | ACCATCCAAC | TTGCTTTGTC | TTCTGCAGAG | AGGAGGCTAA | AGCCCTTGAG | 6 0 |
| CTGGCTGGCA | CTGTACTCAG | GCCGGAAGCC | CAGCTCGTCC | CGGTTCTTGA | CAAAGCAAGT | 1 2 0 |
| TGGATGGTAC | AAGCGG | | | | | 1 3 6 |

( 2 ) INFORMATION FOR SEQ ID NO:10:

( i ) SEQUENCE CHARACTERISTICS:
( A ) LENGTH: 316 base pairs
( B ) TYPE: nucleic acid
( C ) STRANDEDNESS: Not Relevant
( D ) TOPOLOGY: linear ( i i ) MOLECULE TYPE: cDNA ( x i ) SEQUENCE DESCRIPTION: SEQ ID NO:10:

| | | | | | | |
|---|---|---|---|---|---|---|
| TGCCGAGCTG | GGTATTGTGA | CGGTTGATAA | TGGCGGCATC | ATGTTGCCAG | GTACCGGGTA | 6 0 |
| AGCAGACCTC | AGAGCACAGC | TTATTGTCCA | GTGCTTTCAC | GCTCGCGACG | TCAAAGTCAT | 1 2 0 |
| TGTTATTGTC | ACACTCCATG | CCTAGAAATG | CGCATGTCCT | CTGGCCATCT | TCTTGCACAG | 1 8 0 |
| GGGATCTGTC | CTCTTCCTCC | ATGATATCAT | TTCCCTCTGC | ATCCTGCTCT | CCAGCTGGAA | 2 4 0 |
| GGCCAGCAAA | ATTGCTGTCT | GGGGACTCTG | CTGGGGTCTC | CTCCTCTTCT | GAAGGGGCCC | 3 0 0 |
| TGCTAGCAGC | TCGGCA | | | | | 3 1 6 |

( 2 ) INFORMATION FOR SEQ ID NO:11:

( i ) SEQUENCE CHARACTERISTICS:
( A ) LENGTH: 337 base pairs
( B ) TYPE: nucleic acid
( C ) STRANDEDNESS: Not Relevant
( D ) TOPOLOGY: linear ( i i ) MOLECULE TYPE: cDNA ( x i ) SEQUENCE DESCRIPTION: SEQ ID NO:11:

| | | | | | | |
|---|---|---|---|---|---|---|
| AGGGGTCTTG | ATGGACTTGG | GTCGGACATC | TTAGTGACCT | GTGAATTCTT | CTGTGGAGGC | 6 0 |
| TGAGTCTCAC | GTAGCCGAGT | TTAATATCTG | TGCTATTTAC | TAAAGTATCT | GCCACCAAAT | 1 2 0 |

| | | | | | |
|---|---|---|---|---|---|
| TGTACCAACT | CATAGTTTTA | TATGAATGTT | GATGAGTCTG | TATCATAAAT | AGAATTGTTG | 180
| ATACATCCTT | AATTTGTGCA | ATATTGTATG | AAGAAGATTG | TTATCAATTA | AAACCACGCC | 240
| TCTTTATGAT | CCTNNNAAAA | AAAAAAAAAA | AAAAAAAAAA | AAAAAAAAAA | AAAAAAAAAA | 300
| AACCNCCTCA | AATCCATNGG | TTCTAACCCA | AAACCCT | | | 337

( 2 ) INFORMATION FOR SEQ ID NO:12:

( i ) SEQUENCE CHARACTERISTICS:
        ( A ) LENGTH: 307 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:12:

| | | | | | |
|---|---|---|---|---|---|
| TTTTTTTTT | CATACACCAT | CAAACCAATT | TTATTTCTAT | AGCAACGTTT | CTCACGTCTG | 60
| AACCTGAGAA | TAAGTCACCA | GCTCTTGACA | GTAAACATGG | GCCCTATCAA | ATTATATTAG | 120
| ACTCCTCAGT | GTCCGCCAT | GTGGCTTGC | ACCAAATCAA | TTAGTTGAG | GGCCAAAATC | 180
| CTGTTGGGTT | TCAAATAAAG | TGTCAGGTCA | TAAGGAGGGG | GAGGGACTCA | ATTCATGGGA | 240
| ACATTTTTAC | CTGTTCAAAT | AGATAAACTG | AATTGCCCTA | TCTGTGGTCA | CCTGGATCCA | 300
| AGACCCT | | | | | | 307

( 2 ) INFORMATION FOR SEQ ID NO:13:

( i ) SEQUENCE CHARACTERISTICS:
        ( A ) LENGTH: 296 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:13:

| | | | | | |
|---|---|---|---|---|---|
| CCCTGACGAT | AAATGGTAAG | GAACTTTTTT | TTTTTTTTTT | TTTTTTTTTT | TTTTTTTNC | 60
| GAAATAAACA | AACACAGCTT | ATTATTTGGG | GGAACATTAA | NTTCTATAAN | TGAACACAAA | 120
| ANAAAATTAA | NANTTAATGG | GGGGGTANAA | GGGACTTTGA | ATCTATCTGG | TATCATGACA | 180
| TTGAAGCANA | NACCTGANTG | ACCAGAAAGA | GAGAGAGAGA | GAGAGAGAGA | GAGAGAGAGA | 240
| GAGAGGTTTC | ATATGAGCTA | GTGTTACAGG | CTTTATTAGT | CTATTAGTCA | GGGACC | 296

( 2 ) INFORMATION FOR SEQ ID NO:14:

( i ) SEQUENCE CHARACTERISTICS:
        ( A ) LENGTH: 319 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:14:

| | | | | | |
|---|---|---|---|---|---|
| AATCGGGCTG | GATGGGTGTA | TCCGGCACTG | TTTCGTAGCG | GCAGCAACTG | GGTGCTTCTA | 60
| TCTGAAAGCG | GGCTTCACAA | AAACTACTGC | GCCACCCGAC | TCGCTGCGGC | ATCGCCCGGT | 120
| GGCGAGTACC | GTATCGCCTT | TCCTGGTGCA | GAAGAAGTGT | TTACAGGAGG | CGGTCATTTA | 180
| CCGCAATCTG | ATTCTGTTTT | TTATTCTCCC | TGGCGGGTGA | TCGCGATCGG | CAGTTTGAAA | 240
| ACGATCGTTG | AATCCACGCT | CGGGAATGAT | GTGGCTTCGC | CGCCAACGCT | TACTGACATT | 300
| TCATTTGTAC | AGCCCGATT | | | | | 319

( 2 ) INFORMATION FOR SEQ ID NO:15:

( i ) SEQUENCE CHARACTERISTICS:
        ( A ) LENGTH: 287 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:15:

```
GCCGAGCTGT  GTAAAACCAT  CTATCCTCTG  GCAGATCTAC  TTGCCAGGCC  ACTCCCAGGG      60
GGGGTAGACC  CTCTAAAGCT  TGAGATTTAT  CTTACAGATG  AAGACTTCGA  GTTTGCACTC     120
GACATGACCA  GAGATGAATT  CAACGCACTG  CCCACCTGGA  AGCAAATGAA  CCTGAAGAAA     180
GCGAAAGGCC  TGTTCTGAGG  GTGAGATGAC  AGCCACAGAG  AGGTCACTGC  CACTAGACCA     240
GAAAGTGGAT  GGAGATATAT  ATTTGGACTG  GTGTTTTTTT  CTGTCAG                   287
```

( 2 ) INFORMATION FOR SEQ ID NO:16:

( i ) SEQUENCE CHARACTERISTICS:
        ( A ) LENGTH: 344 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:16:

```
ATCGGGCTGC  AGATTGGAGA  CAAGATCATG  CAGGTGAACG  GCTGGGACAT  GACCATGGTC      60
ACTCATGACC  AGGCTCGGAA  GCGGCTCACC  AAACGTTCGG  AGGAAGTGGT  CCGCCTGCTG     120
GTGACTCGGC  AGTCTCTGCA  GAAGGCCGTA  CAGCAGTCCA  TGCTGTCATA  GCTGTAGTCA     180
GCCTAGACTT  CTGCCCACTG  ACCTTTTNGG  GCACTGAGAA  CACATCCACG  CTCTGTCTGT     240
ATCTAGTTCT  GGCTTCTGCT  GTGTGCTANG  CCCCAGCTCT  GAGGAGTAAC  AGCTGATCCC     300
AAAGGTCCAA  GCCAACCTTC  TTACCCCTCA  GCCCCANCC  CGAT                       344
```

( 2 ) INFORMATION FOR SEQ ID NO:17:

( i ) SEQUENCE CHARACTERISTICS:
        ( A ) LENGTH: 300 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:17:

```
TTTTTTTTTT  TTTGGGCAAC  TATGTATTTA  TTGTGTTTGG  AAGGCAGAGT  GAGGGAGGAG      60
ACCCCAGCAG  GAAGAAGACT  GGGTGCAGTC  TAGAGTTCCT  AGTCAAGAGT  AGGAAGGTTT     120
CTGTTATACC  CATCATAGAA  CGAGAGAGGG  GGCTCAATAG  ATCATCCCCT  TTGTCTCTCC     180
ACGGGGCTTC  TTGAGCTTCT  CAAAGTTCTT  CAGGATGATG  TCATATAACA  CAGCATAAGC     240
GTTACGGATC  TCCATGACCA  TCAGCCGGAT  CTCCTGGTAT  TCCGCCTCGT  CCAGCTCGGC     300
```

( 2 ) INFORMATION FOR SEQ ID NO:18:

( i ) SEQUENCE CHARACTERISTICS:
        ( A ) LENGTH: 461 base pairs
        ( B ) TYPE: nucleic acid
        ( C ) STRANDEDNESS: Not Relevant
        ( D ) TOPOLOGY: linear (i i) MOLECULE TYPE: cDNA (x i) SEQUENCE DESCRIPTION: SEQ ID NO:18:

| | | | | | |
|---|---|---|---|---|---|
| AANATCTGCT | TAAAAGTTCT | TTAATTTGTA | CCATTTCTTC | AAATAAAGAA | TTTTGGTACA | 60
| AATTAAAGAA | CTTTTAAGCA | GATGTTTTGG | TGCAACTAAT | AGAAAGATA | AAGGCAGCCT | 120
| GACATGCATG | CACTGCCTCA | GTGACCAGTA | AAGTCACATG | NCCTTGGGAC | GTCAGCTTAG | 180
| NTTTATCACN | GTGTCCCAGG | GGTGCTTGTC | AAAGAGATAT | TCTGCCATGC | CAGATTCAGG | 240
| GGCTCCCATC | TTGCGTAAGT | TGGTCACGTG | GTCACCAGT | TCTTTAATGG | ATTTCACCTG | 300
| CTCATTCAGG | TAATGCGTCT | CAATGAAGTC | ACATAAGTGG | GGATCATTCT | TGTCAGTAGC | 360
| CAGTTTGTGA | AGTTCCAGTA | GTGACTGATT | CACACTCTTT | TCCAAGTGCA | GTGCACACTC | 420
| CATTGCATTC | AGCCCGCTCT | CCCAGTCATC | ACGGTCACNT | A | | 461

(2) INFORMATION FOR SEQ ID NO:19:

(i) SEQUENCE CHARACTERISTICS:
    (A) LENGTH: 280 base pairs
    (B) TYPE: nucleic acid
    (C) STRANDEDNESS: Not Relevant
    (D) TOPOLOGY: linear (i i) MOLECULE TYPE: cDNA (x i) SEQUENCE DESCRIPTION: SEQ ID NO:19:

| | | | | | |
|---|---|---|---|---|---|
| TGACGTAGGG | CCGAGAGCAA | CAAGCACAGA | ACTCCTTCTC | CAGTTTCACC | CTGATGAAGT | 60
| TGAGGCACTC | TTCTGCACTG | GGAGGGGCCA | GCCTGGGGGC | CAGGCACATT | GGACACCACC | 120
| TTCCCATGGA | CTACAGCGTC | AATGCCATTG | CCTTCTATTC | CTATACCTTC | TAGGGGCTGC | 180
| CCCTCTTCCC | ATTCAGCCAA | CACTGAGTGT | TGGGAGATTT | CTCTTTTTA | AAAACACATG | 240
| AGAAATAAA | TGCACTTTAC | TCCCTCCCCA | AAAAAAAAA | | | 280

(2) INFORMATION FOR SEQ ID NO:20:

(i) SEQUENCE CHARACTERISTICS:
    (A) LENGTH: 177 base pairs
    (B) TYPE: nucleic acid
    (C) STRANDEDNESS: Not Relevant
    (D) TOPOLOGY: linear (i i) MOLECULE TYPE: cDNA (x i) SEQUENCE DESCRIPTION: SEQ ID NO:20:

| | | | | | |
|---|---|---|---|---|---|
| GTAGGCAATA | AAATGTTTTC | AGAGGTGCGA | AAAAGCTTTT | GTTTTCTTAA | ACCATTCTTA | 60
| GTCTCTGCCA | CACTTGACAC | TCCGTCAAAG | TGAGAAGCGA | ACTAAAGACC | AACTGCGGTG | 120
| GAAAATATTA | TGTTTATGTA | ATAAAAAAAA | ATCATGTAAC | TGCAAAAAAA | AAAAAA | 177

(2) INFORMATION FOR SEQ ID NO:21:

(i) SEQUENCE CHARACTERISTICS:
    (A) LENGTH: 633 base pairs
    (B) TYPE: nucleic acid
    (C) STRANDEDNESS: Not Relevant
    (D) TOPOLOGY: linear (i i) MOLECULE TYPE: cDNA (x i) SEQUENCE DESCRIPTION: SEQ ID NO:21:

| | | | | | |
|---|---|---|---|---|---|
| TGCCGAGCTG | AAAACATACA | TCCGCACCGG | GTTGAGATAG | CTGGCCCTCC | GTCCCCGGGC | 60
| ATACTCTTTG | GATAAGAACC | CCGGCCTTGT | TACCAGGTAC | CGGAGTGAGC | TGAAAAATTT | 120

| | | | | | | |
|---|---|---|---|---|---|---|
| ACCGTCGAAA | TGGGTGATGT | CCTGGAAAAA | ATGGTTCACC | AGCTGCCAGG | CAGATTCTTT | 180 |
| GGGTTCCACA | TTTTCCTGCC | CACAGATGTG | GCAGAAGCGG | TCAAGTAATG | CAGCATTACA | 240 |
| ATTGAGGCAG | ATCTTTTCTT | TTCTTTCCTT | GGAGTGGCTC | AACCAGCGAT | TTTGGTTAAA | 300 |
| AATAATCAAA | AAAGCGACGG | CAAAACTTTT | GTTATATTCC | CGCCTGTGGC | ATTTGAACTG | 360 |
| TGCCCGGCAA | CCGAATAACT | TTTAATTTTG | AAAATAAAAT | GCATACTAGA | TTTTTAGCGG | 420 |
| TTGCCTCCTG | GCCATTGCTT | CAGGCGCCNG | CACAGCGTCA | GCCCAGTTTT | ACCACNANGA | 480 |
| ATATCCTAAG | CGTTGAAACA | GGGCACAGCC | GAAAAAAACN | CTGGCNACAA | AAAANATCCG | 540 |
| GACATCCTTT | TTCCAATTTT | GAAACCGAAN | GCNCGCAAAC | NAAGGTTCTT | CGGGAAAAAA | 600 |
| AATCGCCAAA | ATACNCGANA | TCAAACTNTC | CAA | | | 633 |

( 2 ) INFORMATION FOR SEQ ID NO:22:

( i ) SEQUENCE CHARACTERISTICS:
        ( A ) LENGTH: 213 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:22:

| | | | | | | |
|---|---|---|---|---|---|---|
| TGCCGAGCTG | GGGGGAGTTC | CAGGAATTTG | TGGACTATTT | CCAGGAGGAA | TTGAGGAATC | 60 |
| TAGAAGTAAT | AAGAACTTCA | CAAGTAGAAC | AACAGAGTTA | ATTGACCTCT | ATCCTTAAGA | 120 |
| GTTACCAGAG | AATTATTAAA | AAACTAAAGA | ACAATCAAAG | CCTGGTCCTG | TGCCACCACC | 180 |
| CAAAAACATG | TATAGCCTAT | GTGCAGCTCG | GCA | | | 213 |

( 2 ) INFORMATION FOR SEQ ID NO:23:

( i ) SEQUENCE CHARACTERISTICS:
        ( A ) LENGTH: 679 base pairs
        ( B ) TYPE: nucleic acid
        ( C ) STRANDEDNESS: Not Relevant
        ( D ) TOPOLOGY: linear ( i i ) MOLECULE TYPE: cDNA ( x i ) SEQUENCE DESCRIPTION: SEQ ID NO:23:

| | | | | | | |
|---|---|---|---|---|---|---|
| CTCANAGGGC | NNNTTNGNGG | NCNTCATGCN | CCAGGNTCCN | NCCCCANAN | GANCNNCCNG | 60 |
| GTAAACTACA | CNGGAGTACT | TAAGTGGACA | NNCCACATGC | GANGGNCAAG | GGGATCACCN | 120 |
| TCNCTCCTNC | AGNCTNTNCG | TGNCTCTCCT | GTNCNTNCAC | TGCCNCANAA | NGGANGCNCN | 180 |
| NNCTCCTATC | TGTNTACAGN | AAACNTGCN | CTNNCTCTAA | GCTCNCCCAC | TNTGTGGAAA | 240 |
| GGCNATGTGT | GCGTGCCTCT | CCCCTATCAC | GGCNGTTTGC | NAAANGGGGA | TGTNCTGCNC | 300 |
| GGCGATGAAG | TTNGGTCACT | CCATGTTTCC | CAGTCCNACC | TGTTAGACNA | AGNATTGNAN | 360 |
| TGTGATACGA | CTCNCTGTAA | GGGGANTNGC | GGACCCAGTA | TGTTTGGCCC | NACNNCCACT | 420 |
| TCTTTAAATG | GTGGCTAACG | GCGCTTCCTA | GNATAAACAC | TATTGGTCCC | CCCCTCTGCA | 480 |
| GNACCCNTTA | CTTCCGNANA | AAAATTGTTG | TCNTGATCCG | CGACAACCAC | ACCGTCTGTN | 540 |
| GNTTTTAGTT | GCAACNCNNA | TCNCTCCAAA | AAAGTTTCAG | AAATCTTCAT | TTTCCNGGT | 600 |
| TGAGCCCNTG | ACAAACCCCT | NAGGATTTGT | CGAATGTAAA | GTCTCCNGAT | CTTCAATAAA | 660 |
| NNTCCAAAAG | NCTANCGAT | | | | | 679 |

( 2 ) INFORMATION FOR SEQ ID NO:24:

( i ) SEQUENCE CHARACTERISTICS:

(A) LENGTH: 717 base pairs
(B) TYPE: nucleic acid
(C) STRANDEDNESS: Not Relevant
(D) TOPOLOGY: linear (ii) MOLECULE TYPE: cDNA (xi) SEQUENCE DESCRIPTION: SEQ ID NO:24:

| | | | | | | |
|---|---|---|---|---|---|---|
| NTCNNCTTNN | CNNNGGCTGA | TATCNGGCNC | TTCNTCCNCG | ATCNCAGATA | CNNGCNCACC | 60 |
| GGNNNTNTCN | GNGGTNATCN | TCCNCCATCT | CTCNTCCCCG | ACNTGCACTC | CGGGTNTNNT | 120 |
| ACACNGGACA | CTGTATCNNA | CAGNAAACCT | NCCCNGGCCC | CAGGGATCAC | CATNCCTCGN | 180 |
| CCCNGCNTGT | NTATAANATC | AGGNNNTACA | TCNANGAACN | NACTATCACN | GNTCTCTNTT | 240 |
| NNCTCAGTGT | NCACCTTCCA | CTNCNGAANC | TNNTCGCTNC | NCCNCNGTTG | GGAAAGGCGA | 300 |
| NCNGTNCCGG | CNACATGCCG | TTTNCGNCNT | CTGNNCACNT | GGGGATCTNC | TNCAANGNAA | 360 |
| TCAATTNGNG | TAACCCACGG | TTTNCNCAAT | CACTACTTCT | CANNCNANGG | CCNTTGAANT | 420 |
| GTTATCCCAC | CACCANGGGG | CNANTCGGGA | CCTNACAATT | CATCCTCAGC | CGGCCCCAGN | 480 |
| CTTAAAAAAT | TCAAAGGNCN | CTTGCCCGCN | TTNTTNCCTT | AGCCCGCCNC | CNGACAACAN | 540 |
| CCNANNAACA | ACCCCCNNTC | TTANGTTGCN | NANCCCACAG | GANNTTGNNA | TACCGGGTTT | 600 |
| CCCCNGAAAC | TNCTCAANGC | CNCCGTTCCA | ACCCCGTTA | CGAAACCGTN | CCCNTTTCCT | 660 |
| TCCGAGNTTG | CCTATTAANN | CCCCCNAAGT | TCTNCTTCGT | TNGNTTCCTC | CGAAANG | 717 |